US006871550B2

(12) United States Patent
Eichmiller

(10) Patent No.: US 6,871,550 B2
(45) Date of Patent: Mar. 29, 2005

(54) POLYMER SHRINKAGE TENSOMETER

(75) Inventor: Frederick C. Eichmiller, Ijamsville, MD (US)

(73) Assignee: American Dental Association Foundation, Chicago, IL (US)

(*) Notice: Subject to any disclaimer, the term of this patent is extended or adjusted under 35 U.S.C. 154(b) by 0 days.

(21) Appl. No.: 10/640,774

(22) Filed: Aug. 14, 2003

(65) Prior Publication Data

US 2004/0154407 A1 Aug. 12, 2004

Related U.S. Application Data

(60) Provisional application No. 60/446,584, filed on Feb. 11, 2003.

(51) Int. Cl.[7] .............................................. G01N 3/008
(52) U.S. Cl. ...................................................... 73/827
(58) Field of Search .......................... 73/826, 827, 828, 73/849, 852, 856, 862.631, 862.632, 862.633, 862.634, 838, 862.636, 862.637

(56) References Cited

U.S. PATENT DOCUMENTS 6,139,053 A * 10/2000 Knox .......................... 280/735
6,508,514 B2 * 1/2003 Wolfe ........................ 297/463.1
6,523,392 B2 * 2/2003 Porter et al. ................ 73/24.01

OTHER PUBLICATIONS

Bowen, R.L., "Adhesive Bonding of Various Materials to Hard Tooth Tissues. VI. Forces developing in direct–filling materials during hardening", J Am Dent Assoc Feb. 1967;74(3):439–445.

Davidson, C.L., de Gee, A.J., "Relaxation of Polymerization Contraction Stresses by Flow in Dental Composites", J Dent Res Feb. 1984;63(2):146148.

Fellzer, A.J.; de Gee, A.J.: Davidson, C.L . . . , "Setting Stress in Composite Resin in Relation to Configuration of the Restoration", J Dent Res Nov. 1987; 66(11)1636–1639.

Fellzer, A.J.; de Gee, A.J.; Davidson, C.L., "Relaxation of Polymerization Contraction Shear Stress by Hygroscopic Expansion", J Dent Res Jan. 1990;69(1)36–39.

Watts, D.C., Cash, A.J., "Determination of Polymerization Shrinkage Kinetics in Visible–Light Cured Materials: Methods Development", Dent Mater Oct. 1991;7(4):281–287.

Watts, D.C.; Marouf, A.S.; Al–Hindl, A.M., "Photo–Polymerization Shrinkage–Stress Kinetics in Resin–Composites: Methods Development", Dent Mater Jan. 2003;19(1):1–11.

Katona, T.R., Winkler, M.M., "Stress Analysis of a Bulk–Filled Class V Light–Cured Composite Restoration", J Dent Res Aug. 1994;73(8)14701477.

Kinomoto, Y, Torii, M., "Photoelastic Analysis of Polymerizatin Contraction Stresses in Resin Composite Restorations", J Dent Mar. 1998;26(2):165–171.

Sakaguchi, R.L., Ferracane. J.L., "Stress Transfer From Polymerization Shrinkage of a Chemical–Cured Composite Bonded to a Pre–cast Composite Substrate", Dent Mater 1998;14(2):106–111.

* cited by examiner

*Primary Examiner*—Max Norri
(74) *Attorney, Agent, or Firm*—Banner & Witcoff, Ltd.

(57) ABSTRACT

An apparatus and method for measuring the characteristics of curing polymers. The apparatus and method utilize cantilever beam technology to determine characteristics of polymers during the curing process, including but not limited to, stress-related forces that develop during the polymer curing process. The apparatus and method also provide for controlling and monitoring environmental conditions during the curing process.

80 Claims, 18 Drawing Sheets

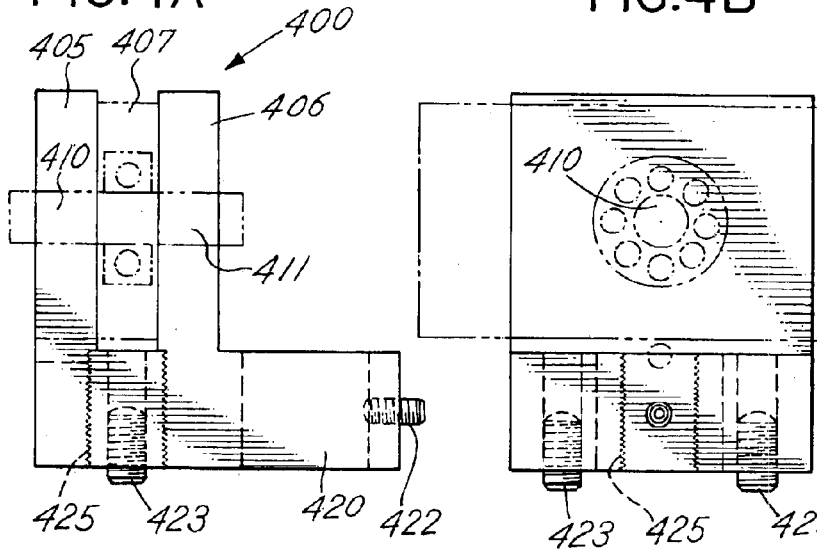

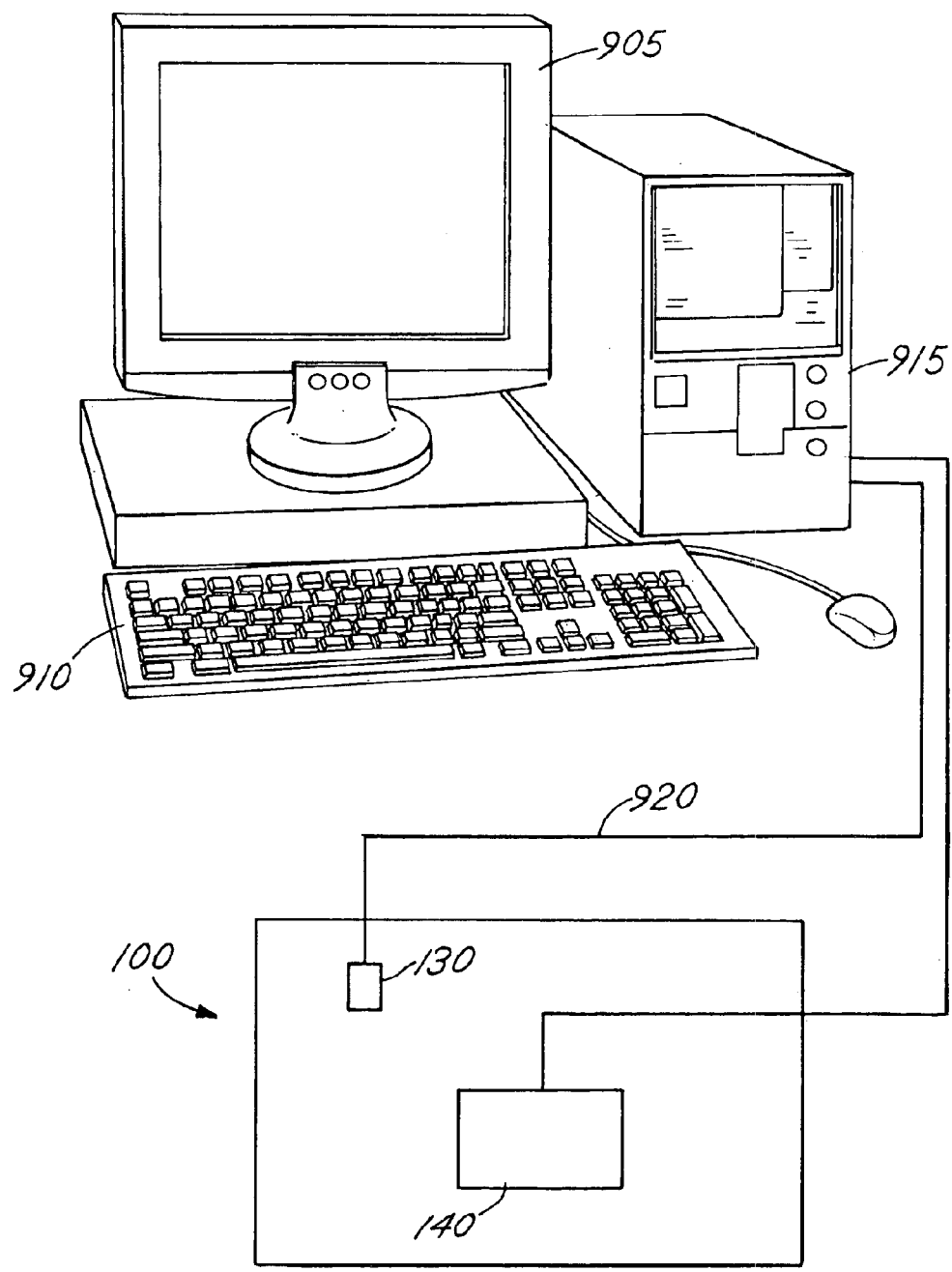

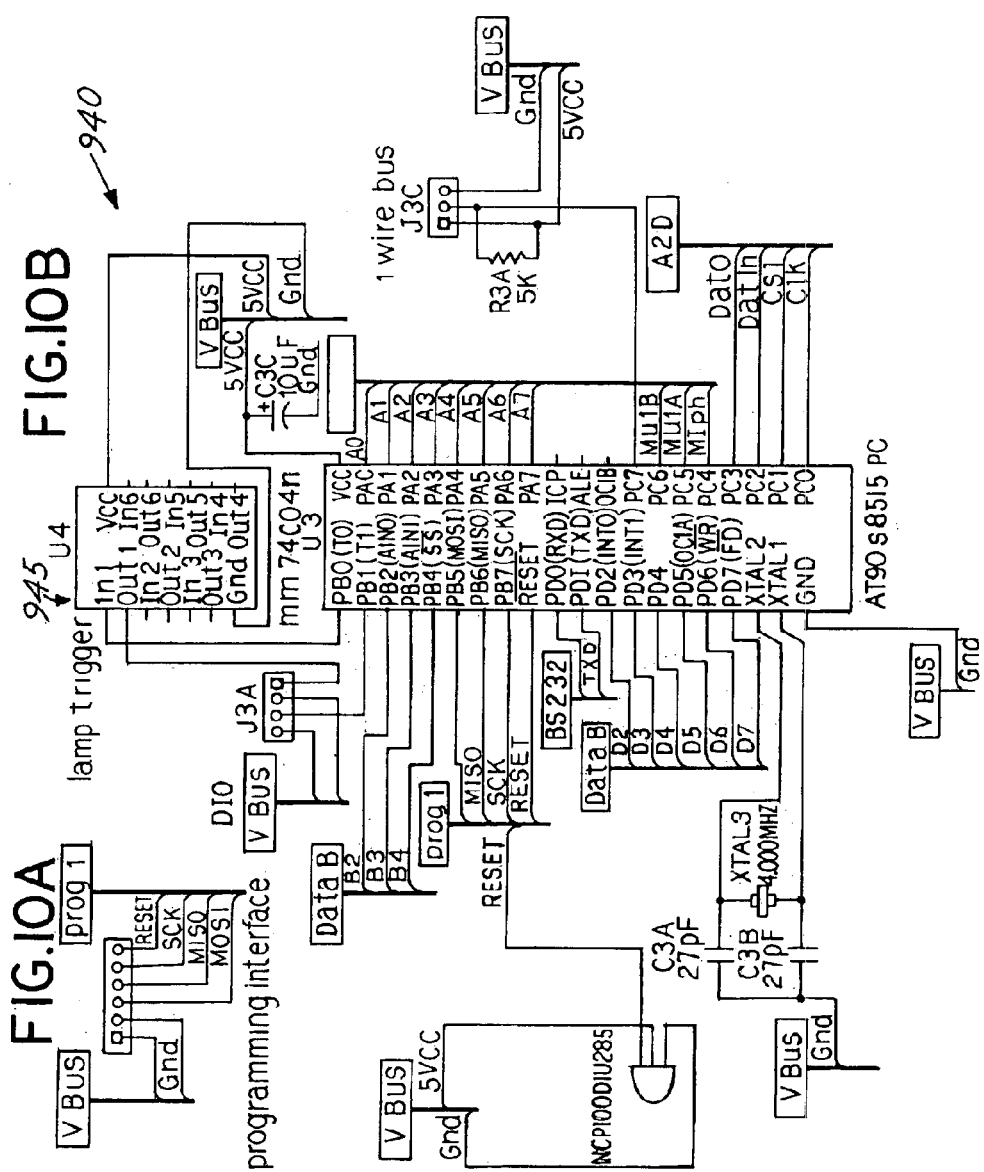

5V and -5V power

DIVIDE REFERENCE VOLTAGE SPAN WITH THERMISTOR AND A KNOWN RESISTOR ROUGHLY THE SAME SIZE AS THE THERMISTER RESISTANCE

USE JUMPERS AS NEEDED

LVDT voltage divider

LVDT voltage clamp

Make 2.5V from 5V
and −2.5V from 5V

POLYMER SHRINKAGE TENSOMETER

CROSS REFERENCE TO RELATED APPLICATIONS

This application claims the benefit of U.S. Provisional Application No. 60/446,584, filed Feb. 11, 2003, titled "Polymer Shrinkage Tensometer" by Frederick C. Eichmiller which is incorporated herewith by reference and for which priority is claimed.

STATEMENT REGARDING FEDERALLY SPONSORED RESEARCH OR DEVELOPMENT (Not applicable)

FIELD OF THE INVENTION

This invention relates generally to the measurement of characteristics of curing polymers. More particularly, this invention relates to the measurement of stress-related forces and displacements that develop during the polymer curing process, for example during the curing of dental polymer material.

BACKGROUND OF THE INVENTION

Polymerization shrinkage is one of the major deficiencies in dental polymers. Public and private research groups are expending considerable effort to develop materials and methods to reduce this shrinkage. The researchers require accurate, reproducible and pertinent measurements of shrinkage properties to assess the effectiveness of their developments. Researchers have developed several methods to assess the stress developed by dental filling composites as they shrink, but none of these previously developed methods have the ability to rapidly and accurately track stress in real-time under conditions approximating those of actual clinical use. Thus, there exists a great need in the art for an apparatus and method that overcome the deficiencies of prior methods and provide for measuring temporal stress development under curing and load conditions similar to those found in actual clinical use.

Such an apparatus and method is ideally capable of varying load and compliance settings to approximate the dynamic displacement occurring in teeth as dental fillings harden. Practitioners can use these settings to compare process parameters such as material composition, curing methods, surface area to volume ratio, and curing dynamics in real-time using samples that are similar in volume to dental fillings. Such an apparatus and method should provide for rapid loading and analysis of samples. Such an apparatus and method should also be automated to allow for rapid run condition and data collection, graphing and analysis. Such an apparatus and method will have utility for research and development of improved dental composites and any polymer where shrinkage and stress are important factors. Such an apparatus can also be used for research and development of improved initiator systems and curing devices. Such an apparatus and method could also be used in a manufacturing setting for polymer and composite quality assessment.

Many researchers have attempted to develop an apparatus and method for measuring polymerization shrinkage stress, but no researcher has yet developed an apparatus and method that is versatile enough to mimic clinical conditions and environmental conditions of clinical use. For example, Bowen provided the first reported description of a method for measuring shrinkage (Bowen R L, Adhesive bonding of various materials to hard tooth tissues. VI Forces developing in direct-filling materials during hardening. *J Am Dent Assoc* 1967 February;74(3):439–445). Bowen's method included placing samples between two platens of an Instron Universal Testing Machine. A load cell attached to the upper platen measured the load generated as the sample cured and shrank. A Tuckerman optical interferometer measured the displacement of the platens, and an operator manually adjusted the Instron crosshead to compensate for this displacement. Using this method, the practitioner calculated stress from the measured load and sample area and plotted the stress vs. time during the curing process.

The Bowen method is deficient, because the method involves measuring stress developing under near zero strain, since the practitioner compensates for the strain by manually adjusting the crosshead during the curing process. The condition maintained by the practitioner does not simulate the conditions that occur in clinical situations where teeth bend as the shrinkage stress increases. Bowen's method does not provide for mimicking the strain experienced in teeth. Bowen's method also does not provide for introducing other environmental factors to the test, such as light curing, water sorption, and convenient adjustment of bonded area/volume ratio (C-factor). Bowen's method also requires the tedious manual adjustment of crosshead position via manual movement of the crosshead drives.

Davidson improved upon Bowen's method (Davidson C L, deGee A J, Relaxation of polymerization contraction stresses by flow in dental composites. *J Dent Res* 1984 February;63(2):146148) by adding an automated feedback transducer to perform the crosshead adjustment. Feilzer, in turn, added the ability to change the C-factor by adjusting the sample diameter and thickness and also added the ability to light cure the material (Feilzer A J, de Gee A J, Davidson C L, Setting stress in composite resin in relation to the configuration of the restoration. *J Dent Res* 1987 November;66(11)1636–1639). The method still, however, did not simulate the strain experienced in teeth during the curing of a filling. Additionally, specimens often fractured during testing due to the feedback requirement to maintain near zero specimen strain.

Many have adopted the Bowen/Davidson/Feilzer methodology, but none have resolved the problems of simulating tooth strain or of specimen fracture during testing. Also, none have adapted the methodology to provide for the addition of environmental factors, such as temperature change or water sorption.

Feilzer also introduced a method that involved measuring the curvature of a glass slide that was bent by the shrinkage stress of a composite sample bonded to one side of the slide (Feilzer A J, de Gee A J, Davidson C L, Relaxation of polymerization contraction shear stress by hygroscopic expansion. *J Dent Res* 1990 January;69(1)36–39). The method provided for determining stress by calculating the tangential bending stress of the slide to determine a maximum shear stress occurring at the ends of the sample strips. The experimental conditions, however, did not mimic in any way the strain conditions experienced in clinical settings where stresses are primarily wall-to-wall tensile stresses. The method also does not provide for adjusting the C-factor to be clinically relevant to bonded dental fillings.

Watts described a method similar to Feilzer's, involving a disc-shaped specimen cured between two glass plates (Watts D C, Cash A J, Determination of polymerization shrinkage kinetics in visible-light cured materials: methods development. *Dent Mater* 1991 October;7(4):281–287). The method included measuring the glass deflection to determine the kinetics of shrinkage volume change, but did not include stress measurements.

Watts described a second method of determining shrinkage stress using a cantilever beam shrinkage-stress kinetics in resin-composites: methods development, *Dent Mater* 20003 January;19(1):1–11). The cantilever beam deflection was measured with an attached strain gauge as the sample shrinkage pulled the beam downward. The sample was also attached to a load cell to record load generation during shrinkage. A correction factor was then applied to the raw stress values to normalize the data in an approximation to what were considered to be the expected stresses. The device was claimed to be useful for both light cured and chemically cured materials. One deficiency of the device was that it was designed with a fixed compliance and it did not have the ability to vary stiffness to simulate the different stress/strain characteristics of different tooth-restoration configurations. The device also required an estimated correction factor multiplier of 4 to arrive at the reported stress values derived from the beam deflection and load cell. The sample geometry could not simulate the bonded/unbonded area ratio found in tooth restorations and often used in these types of experiments and no provisions were made for monitoring the onset and completion of light curing during the measurement process. The device described did not provide for introducing environmental variables such as water sorption or temperature changes. No provisions were made for rapid sample loading and no direct calibration method was incorporated into the instrument design.

Researchers have also utilized finite element modeling to calculate stress development during shrinkage (Katon T R, Winkler M M, Stress analysis of a bulk-filled class V light.cured composite restoration. *J Dent Res* 1994 August;73(8)14701477). Finite element modeling methods can theoretically model two and three-dimensional filling configurations, but the stress values obtained are based upon engineering equations and assumptions of the basic mechanical properties of the materials and the substrates. Finite element modeling does not involve the testing of actual samples.

Researchers have also used photoelastics to determine stress locations and relative amount of stress in simulated fillings (Kinomoto Y, Torii M, Photoelastic analysis of polymerization contraction stresses in composite restorations. *J Dent* 1998 March;26(2):165–171). Again, no direct stress or load measurements are made using these methods, and interpretation relies upon assumptions of material and substrate properties. Also, the photoelastic models required do not have stress/strain relationships similar to real teeth.

Sakaguchi introduced a strain gauge method that combined finite element modeling with strain measured by embedded strain gauges in a sample (Sakaguchi R L, Ferracane J L, Stress transfer from polymerization shrinkage of a chemical-cured composite bonded to a pre-cast composite substrate. *Dent Mater* 1998;14(2):106–111). The method provided for tracking stress kinetics, but was not versatile enough to provide for varying the C-factor or include many of the clinically relevant factors, such as thermal expansion or water sorption. The method also did not provide for simulating the strain conditions reported in the literature for composite shrinkage in tooth cavities.

All of the methods and apparatus previously described in the literature fail to provide a quick, convenient, and clinically relevant method of determining shrinkage stress.

SUMMARY OF THE INVENTION

The present invention overcomes the limitations discussed with respect to prior efforts by providing an apparatus and method that can be readily adapted to simulate the stress/strain conditions of various cavity preparations and sizes. The apparatus and method provide for rapidly and reproducibly establishing a wide range of C-factors, and controlling environmental test conditions such as temperature, light, and water sorption. The apparatus and method also provide for reduced specimen failure during the measurement process. The apparatus and method do not require sophisticated testing equipment and can be practiced using simple bench-top apparatus. The apparatus and data acquisition system are capable of simultaneously monitoring sample strain, sample load, sample stress, the onset and completion of light curing, and sample temperature.

An aspect of the present invention provides a cantilever beam of adjustable length, which enables variance of the load rate under which a polymeric sample is tested. The load-to-displacement ratio can be increased by shortening the cantilever length of the beam by sliding the beam into a mounting block. Conversely, the load-to-displacement ratio can be decreased by lengthening the cantilever length of the beam by sliding the beam out of the mounting block or by sliding the sample collet holder along the length of the fixed beam.

Another aspect of the invention provides a test fixture including two collets, one mounted near the free end or on a sliding holding fixture that can be located along the length of the cantilever beam and the other mounted to a reference base. Cylindrical rods, made from materials to which the polymeric test material can adhere, are placed in each collet with the ends spaced a distance apart corresponding to the length of the sample to be tested. The diameter of the rods can be varied by using collet inserts of various size.

A further aspect of the invention provides for measuring cantilever beam movement with an electronic position transducer as the test sample cures. The transducer is coupled to the reference base and the cantilever beam such that the transducer measures the relative position between the cantilever beam and the reference base or displacement between the upper collet and the reference base. A micrometer coupled between the transducer and the reference base allows setting the transducer configuration to the most desirable operating point. Once the starting position is set and the test sample begins to cure, the transducer measures movement between the cantilever beam and reference base, and thus between the two collet inserts. Movement between the cantilever beam and the reference base results in a change in electric potential output from the transducer. A measurement monitor records the transducer output as a function of time and performs calculations to convert the change in electrical potential to distance, load or stress. Alternately, the transducer can be fixed to the reference base near the end of the beam. Other methods of measuring beam deflection could include strain gauges or other optical or mechanical measurement methods.

A still further aspect of the invention provides a curing activation device to facilitate curing of the test sample. The measurement monitor may be coupled to the curing activation device to control operation thereof. A detection device, such as a phototransistor or photoresistor can be incorporated into the upper collet to detect the onset and completion of curing activation. In addition, sample temperature can be monitored during and after curing by incorporating a thermocouple or thermistor into the sample and monitoring during the measurement. Additional features, such as a water jacket surrounding the sample or a thermally controlled chamber surrounding the sample could be added to introduce different environmental conditions during the measurement.

BRIEF DESCRIPTION OF THE DRAWINGS

In the detailed description that follows, reference will be made to the drawing comprised of the following figures:

FIGS. 4A–4C show frontal, side and top views of an upper test fixture bracket.

FIG. 9 is a drawing illustrating a measurement monitor interfaced to testing apparatus.

FIGS. 10A–10L contain schematics for tensometer electrical circuits.

DESCRIPTION OF THE PREFERRED EMBODIMENT

In the following detailed description, spatially orienting terms are used, such as "upper," "lower," "left," "right," "vertical," "horizontal," and the like. It is to be understood that these terms are used for convenience of description of the preferred embodiments by reference to the drawings. These terms do not necessarily describe the absolute location in space, such as left, right, upward, downward, etc., that any part must assume.

Figure 1:
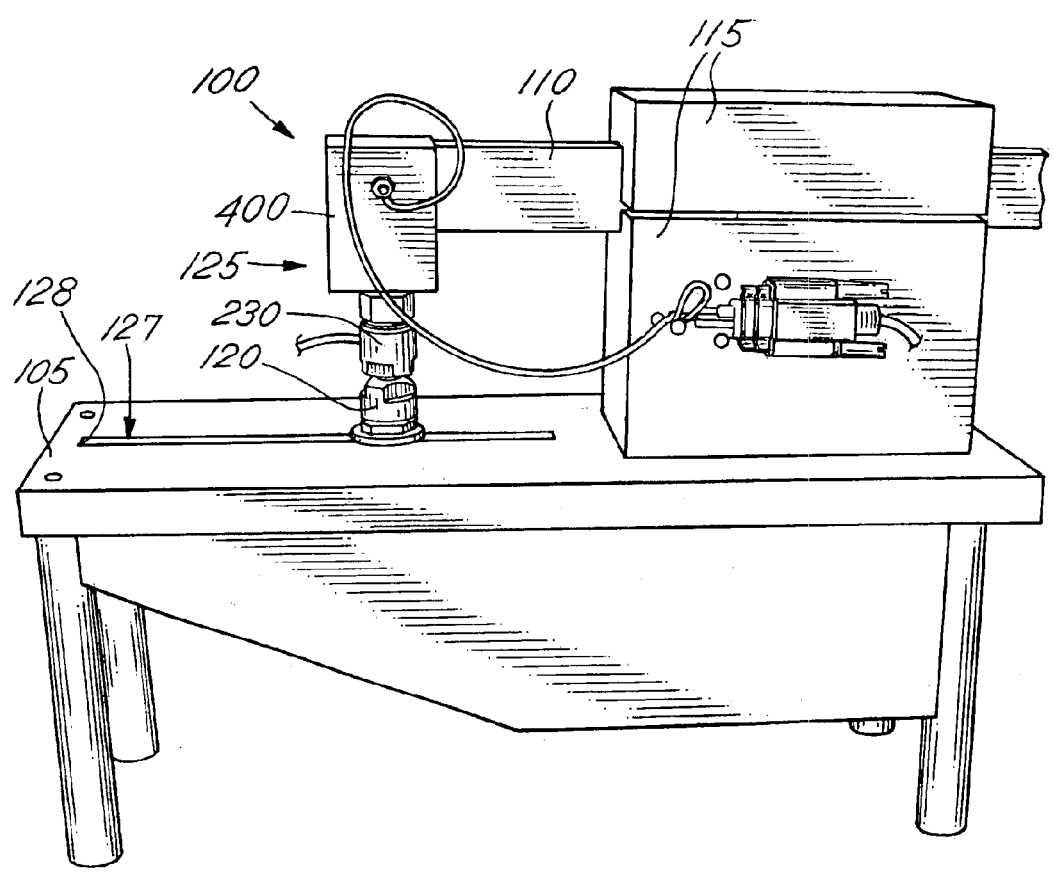
FIG. 1 is a frontal elevated view of a polymer shrinkage tensometer incorporating aspects of the present invention.
Figure 2A:
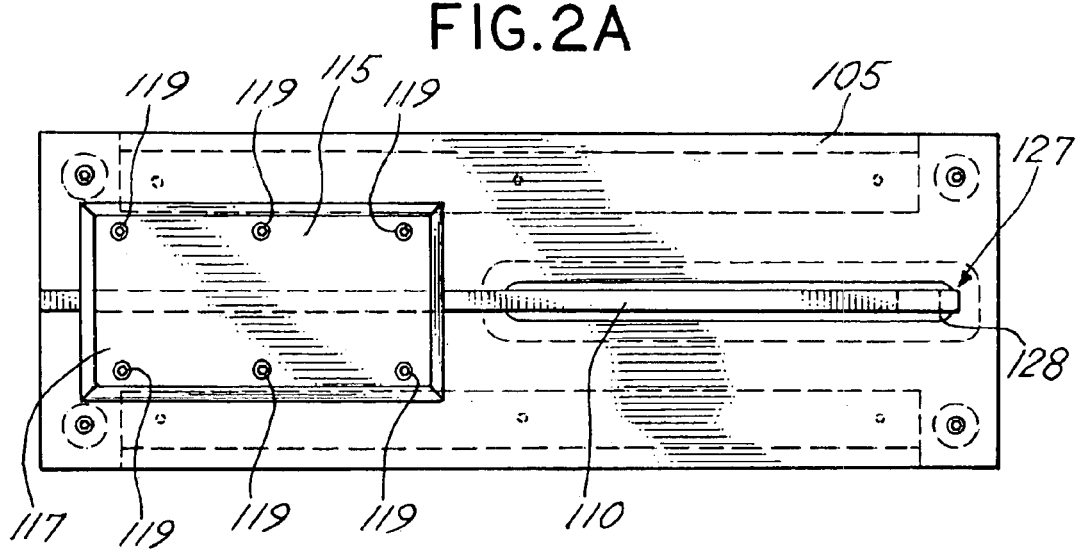
FIGS. 2A–2D show top, side, bottom and frontal views of the basic structure of the tensometer.
Figure 2B:
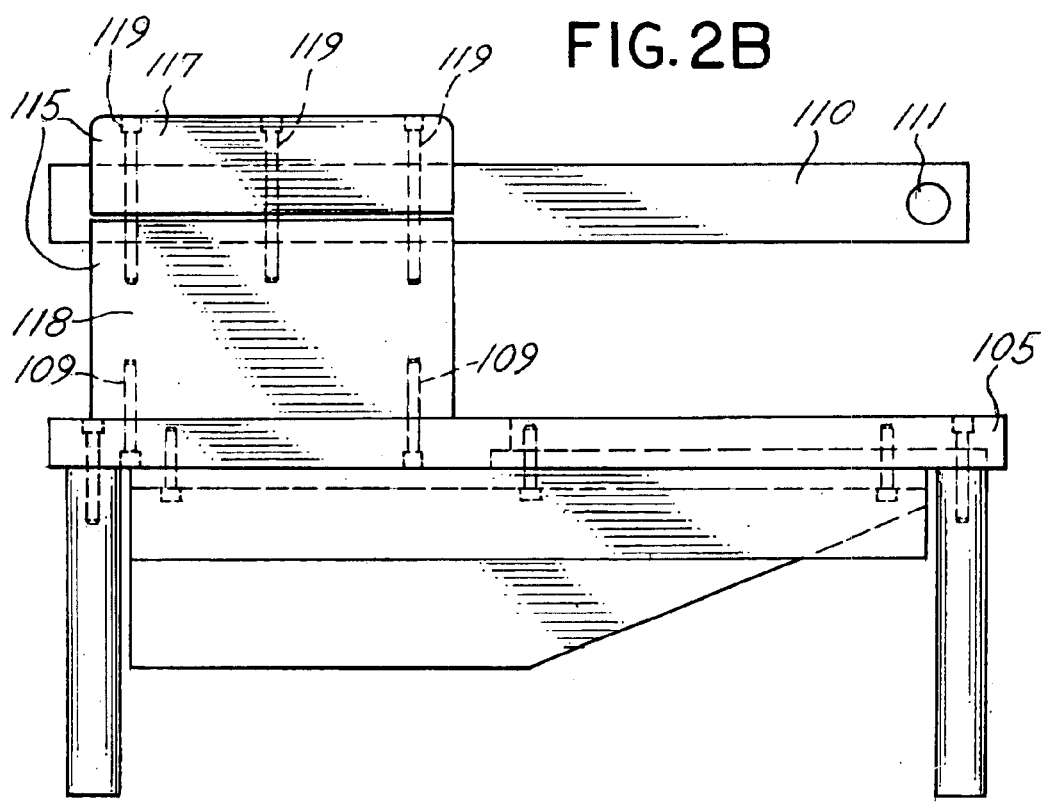
Figure 2C:
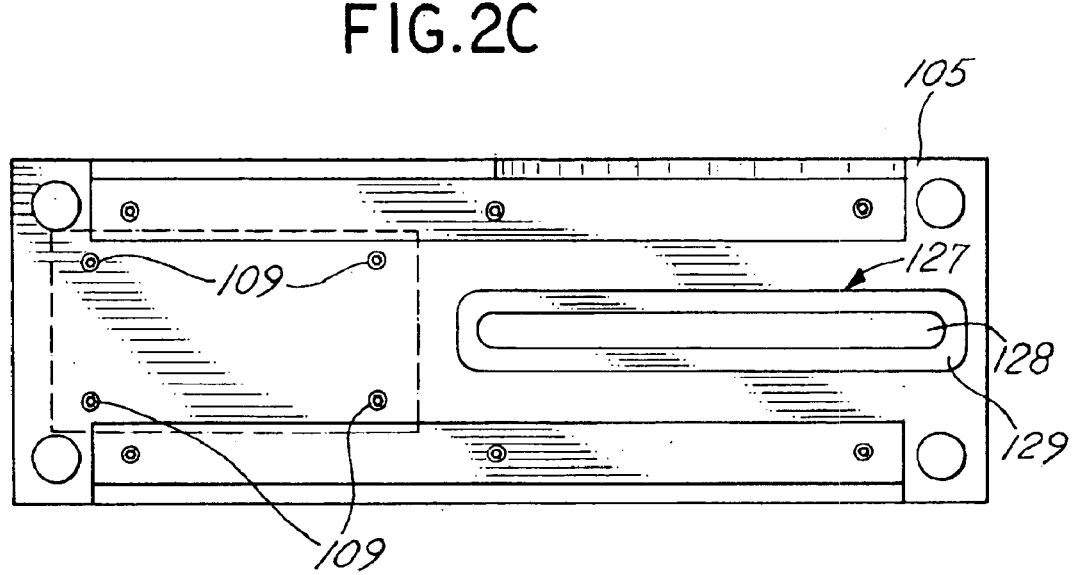
Figure 2D:
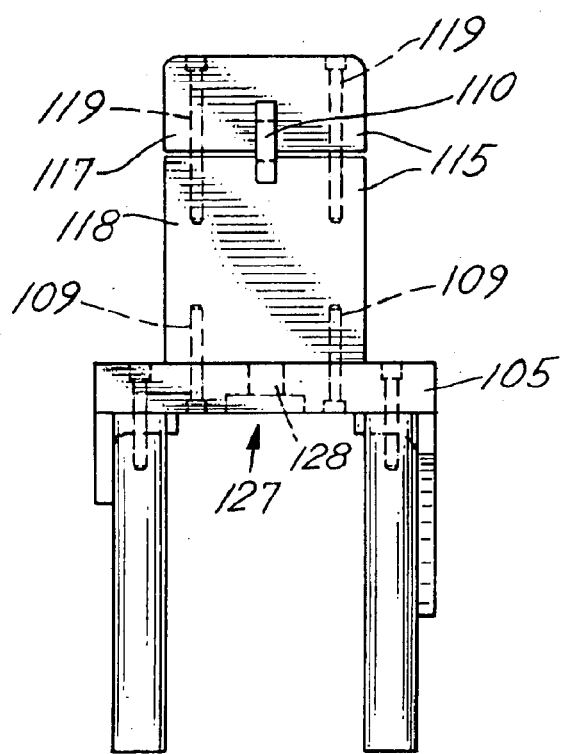
Figure 3A:
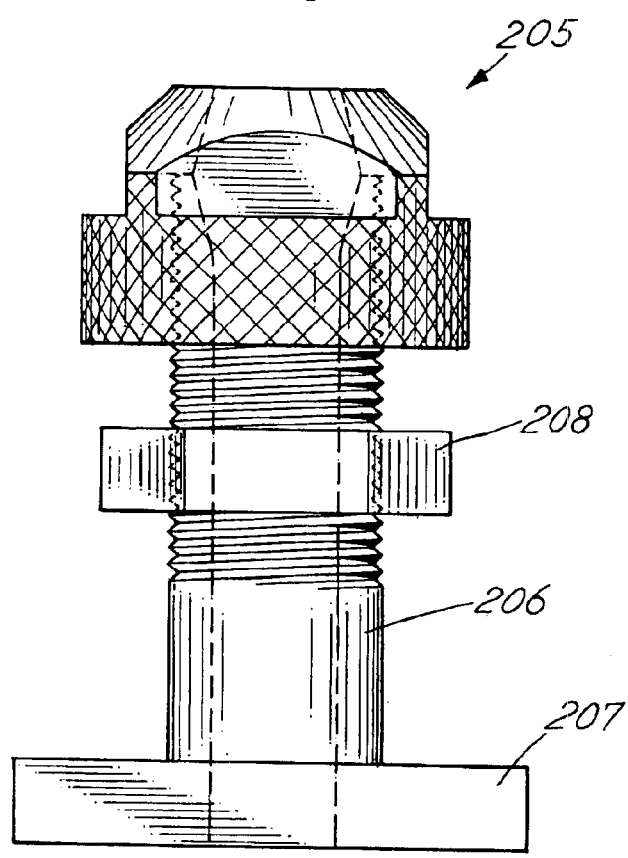
FIGS. 3A–3B show side and top views of a lower collet.
Figure 3B:
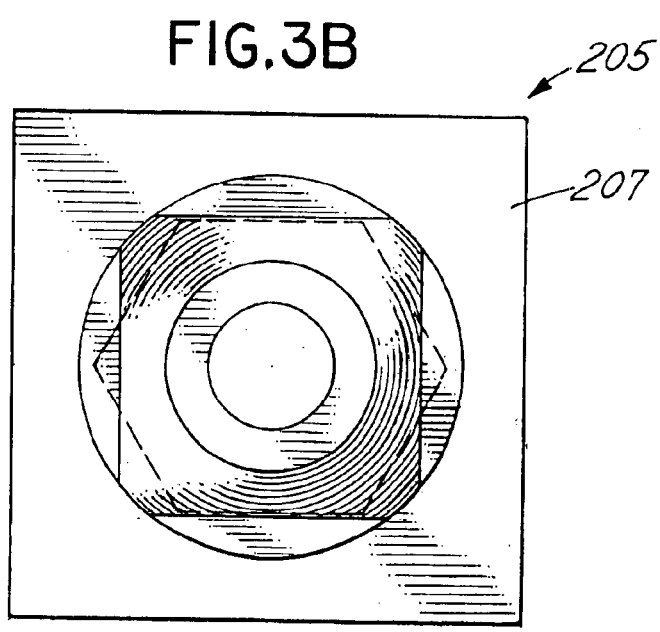

FIG. 1 is a frontal elevated view of a polymer shrinkage tensometer 100 incorporating aspects of the present invention. FIGS. 2A–2D contain drawings of basic structural features of the tensometer 100. Referring to FIGS. 1 and 2A–2D, the tensometer 100 includes a reference member 105, beam member 110, beam mount 115, lower test fixture member 120, and upper test fixture member 125.

The reference member 105, also referred to as the reference base 105, serves as a point of reference for beam position measurements. The reference member 105 is preferably stationary and substantially immobile, but may also take the form of a flexible beam in an alternate embodiment. The reference member 105 includes a fixture translation feature 127, which in the illustrated tensometer 100 includes a slot 128 running along the reference member 105 in a direction substantially parallel to the longitudinal axis of the beam member 110. The fixture translation feature 127 may assume a variety of forms, for example, a groove cut into the reference member 105, a ridge protruding from the reference member 105, or a rail attached to the reference member 105.

A lower fixture member 120 is coupled to the reference member 105 using the fixture translation feature 127. In the illustrated tensometer 100, the lower test fixture member 120 includes a lower collet 205, which is illustrated in detail in FIGS. 3A–3B. With reference to FIGS. 2A–2D and 3, the shaft 206 of the lower collet 205 extends upward through the slot 128 of the fixture translation feature 127. The base lip 207 of the lower collet 205 contacts the land 129 around the slot 128 of the fixture translation feature 127. The lower collet nut 208 is loosened to allow the lower collet 205 to translate along the length of the fixture translation feature 127, and is tightened to secure the lower collet 205 at the desired location along the fixture translation feature 127 for testing.

Referring now to FIGS. 1 and 2A–2D, the beam mount 115 couples the beam member 110 to the reference member 105. The beam mount 115 is coupled to the reference member 105 with mounting screws 109. The beam mount 115 utilizes a clamping mechanism that, when loose, allows the beam member 110 to slide in and out of the beam mount 115 along the longitudinal axis of the beam member 110 or to replace the beam with beams of different stiffness. When tight, the clamping mechanism of the beam mount 115 locks the beam member 115 in place relative to the reference member. As shown most clearly in FIG. 2B, the illustrated beam mount 115 includes an upper beam mount half 117 and a lower beam mount half 118. Six screws 119 provide the clamping force between the upper beam mount half 117 and the lower beam mount half 118. The beam mount 115 illustrated and shown in the attached Figures is only one of a multitude of possible beam mount configurations that could couple the beam member 110 to the reference member 105. The beam mount 115 preferably provides for adjustment of the cantilever length of the beam member 110 (i.e., the portion of the beam member 110 that will move in relation to the reference member 105 in response to forces provided by a curing test sample) and for convenient replacement of beam members 110 made from materials of differing stiffness.

The upper test fixture member 125 is coupled near the end of the cantilever portion of the beam member 110. The upper test fixture member 125 may be mounted to the beam member 110 using the upper test fixture mounting hole 111 in the beam member 110. The upper test fixture member 125 may include an upper test fixture bracket 400 as shown in detail in FIGS. 4A–4C. Referring to FIGS. 4A–4C, the upper test fixture bracket 400 includes two clevis prongs 405, 406 and a clevis opening 407 to accommodate the beam member 110. The upper clevis prongs 405, 406 include mounting holes 410, 411 to accommodate hardware for mounting the upper test fixture bracket 400 to the beam member 110. The upper test fixture bracket 400 also includes beam member set screws 423 for securing the upper test fixture bracket 400 to the beam member 110. An alternative method is for the clevis prongs 405 and 406 to be horizontally connected across the top so as to wrap completely around the beam member 110 so that it can slide along the length of the beam member 410 and be secured at any location using the setscrews 423. The upper test fixture bracket 400 further includes a measuring device mounting hole 420 and corresponding setscrew 422, and a threaded collet mounting hole 425. An alternative method would be to mount the measuring device directly to the reference base 105.

Figure 5A:
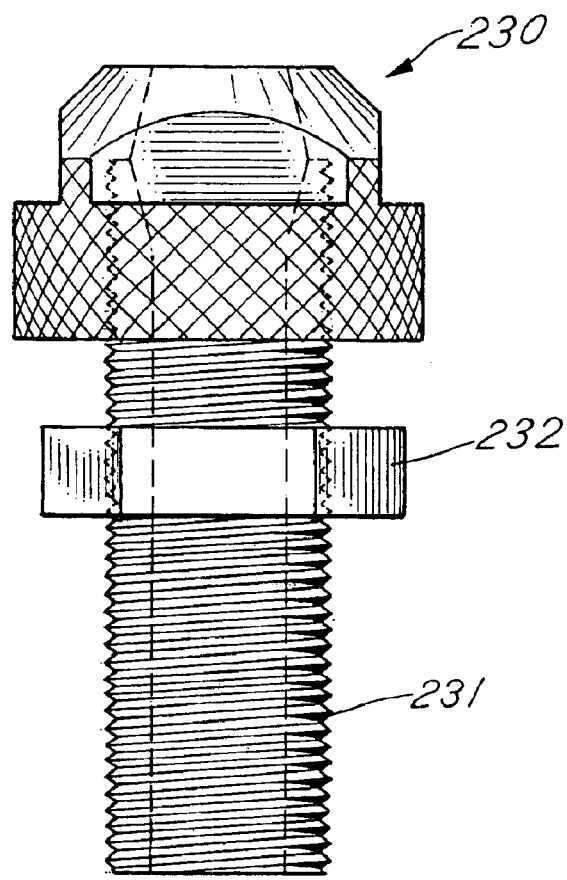
FIGS. 5A–5B show side and top views of an upper collet.
Figure 5B:
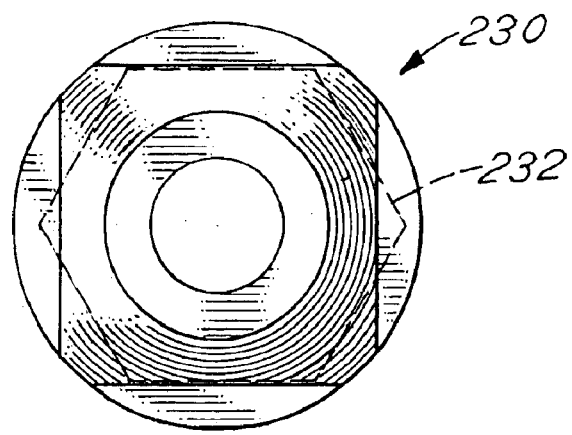

Referring back to FIG. 1, the upper test fixture member 125 includes an upper collet 230 coupled to the upper test fixture bracket 400. FIGS. 5A–5B show detailed drawings of the upper collet 230. The upper collet 230 and lower collet 205 can be configured to accommodate standard machine collet inserts of varying diameters. The upper collet 230 is coupled to the upper test fixture bracket 400 by screwing the threaded end 231 of the upper collet 230 up into the threaded collet mounting hole 425 of the upper test fixture bracket 400. The upper collet 230 is then secured to the upper test fixture bracket by tightening the upper collet mounting nut 232 against the upper test fixture bracket 400. The upper test fixture bracket 400 can also be configured to hold a cure monitoring device, such as a phototransistor or photoresistor above and in line with the center of upper collet 230.

Figure 6:
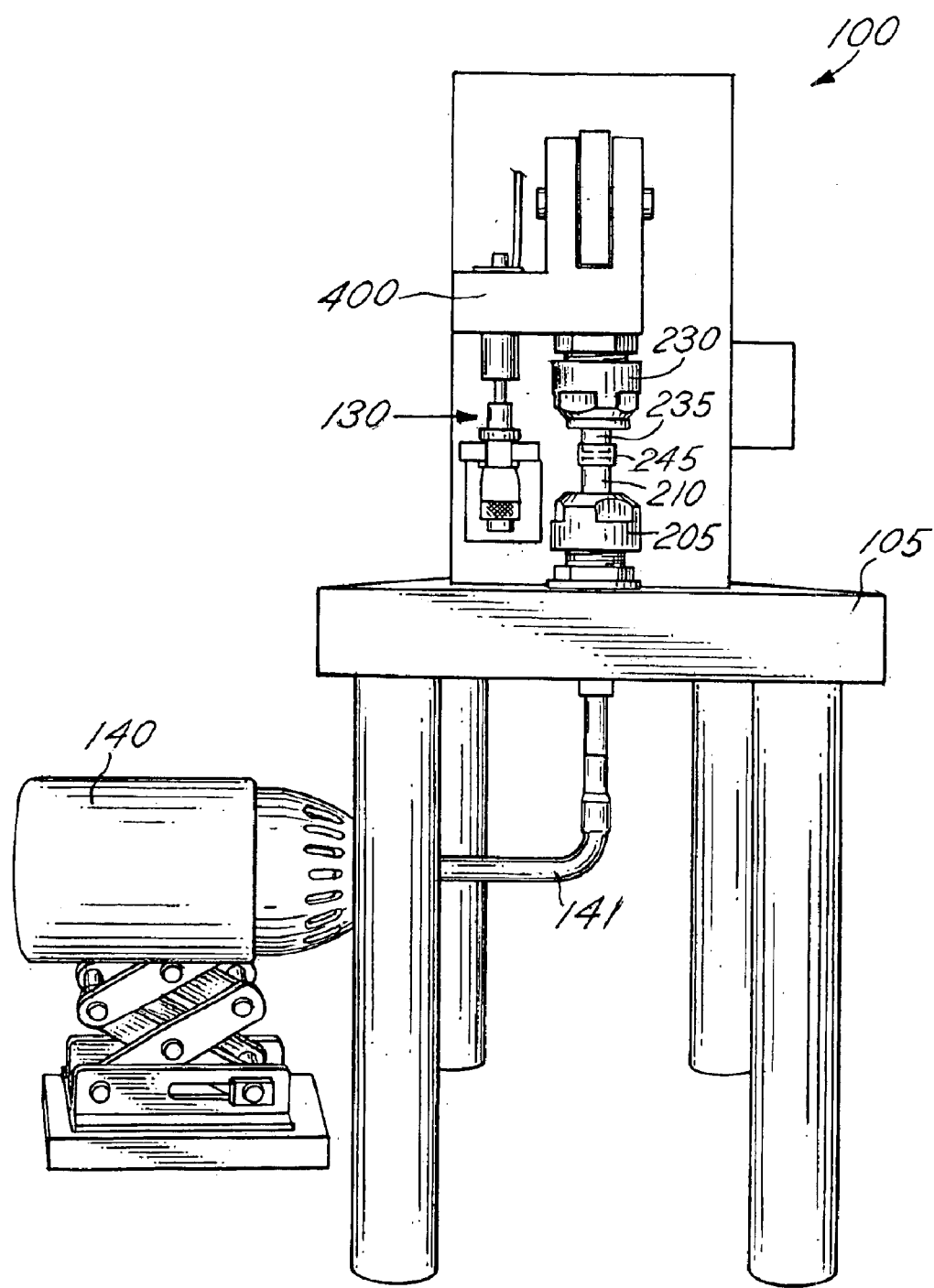
FIG. 6 shows a side view of the tensometer of FIG. 1.
Figure 7:
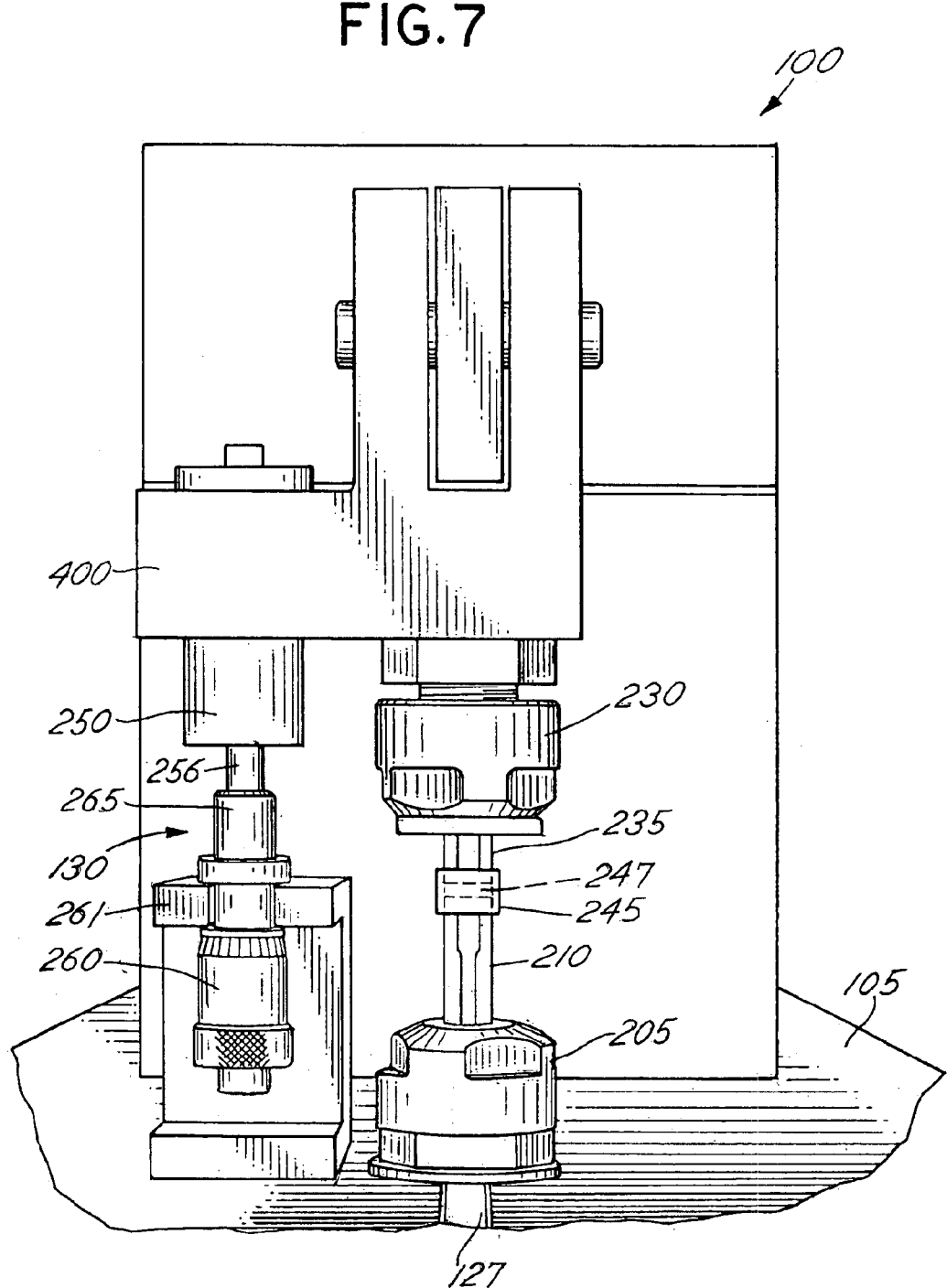
FIG. 7 is an enlarged view of test fixture member apparatus and beam position measuring apparatus.

FIG. 6 is an end view of the tensometer 100 of FIG. 1, and FIG. 7 is an enlarged end view of a portion of the tensometer 100. Referring to FIGS. 6 and 7, the upper collet 230 is coupled to the upper test fixture bracket 400. The lower collet 205 is coupled to the reference member 105, preferably using the fixture translation feature 127 discussed previously.

An upper rod 235 is inserted into and secured by the upper collet 230. A lower end of the upper rod 235 protrudes downward from the upper collet 230 and has a lower end face. A lower rod 210 is inserted into and secured by the lower collet 205. The upper end of the lower rod 210 protrudes upward from the lower collet 205 and has an upper end face. The upper end face of the lower rod 210 and the lower end face of the upper rod 235 are in a generally opposed and spaced relation with a gap between them. The opposed and spaced rod ends are preferably of a material to which a polymer material under test adheres, but may also be of a material that can be treated to facilitate the adherence of polymer material thereto.

The upper end face of the lower rod 210 and the lower end face of the upper rod 235 generally make up a lower test fixture surface and an upper test fixture surface, respectively. It is to be noted that though in the illustrated embodiment, the opposed end faces of the lower rod 210 and upper rod 235 make up the lower test fixture surface and the upper test fixture surface, respectively, the upper and lower test fixture surfaces may take many alternative forms. For example, the upper and lower test fixture surfaces may be contoured, flat, convex, concave or any combination thereof. During polymer testing, curing polymer generally resides in the space between the lower and upper test fixture surfaces. In the illustrated embodiment, the curing polymer generally resides between the upper end face of the lower rod 210 and the lower end face of the upper rod 235.

A mold member may be provided to further govern the location of the polymer test material. Referring to FIGS. 6 and 7, an exemplary mold member 245, particularly suited to the illustrated embodiment, includes a length of flexible tubing disposed about the upper rod 235 and the lower rod 210. The flexible tubing of mold member 245, upper surface of the lower rod 210 and lower surface of the upper rod 235 form a test sample cavity 247 for encapsulation of a polymer test sample. The flexible tubing of the mold member 245 may, for example, be matched to the rods 210, 235 such that the inner diameter of the flexible tubing is matched to the outer diameter of the upper and lower rods 235, 210, thus allowing for relative motion between the upper and lower rods 235, 210 during polymer test sample curing, while serving the function of controlling radial spread of the polymer test sample. Alternatively, the mold material could be made of a material that will not adhere to the test material or to the upper rod 235 and or lower rod 210. Of course, many alternative configurations of the mold member 245 would sufficiently hold the polymer test sample during the curing process.

In another aspect of the present invention, the mold member 245 may include a split cell, such that a first portion of the cell would contain the polymer test sample, and a second portion of the cell would serve to contain environmental control material. Such environment material may include, for example, air or fluid at a particular temperature, or air with a particular moisture content. A wall between the first and second portions of the split cell may be of a material that allows the passage of temperature and moisture between the first and second portions of the split cell without allowing the passage of the polymer test sample.

The mold member 245 can also have one or more holes located at the level of the test sample cavity 247 through which the sample can be inserted by injecting, for the venting of air from the sample cavity 247, and through which a temperature monitoring device, such as a thermocouple or thermistor can be introduced into the sample. Other devices, such as fiber optic monitors could also be introduced using this method.

FIGS. 6 and 7 further illustrate a curing activation device 140 aspect of the present invention. The curing activation device 140 may be, for example, a dental curing light. The curing activation device 140 provides curing energy to facilitate the curing of a polymer test sample during testing. A curing energy coupling 141, such as a fiber optic tube, may deliver the curing energy from the curing activation device 140 to the polymer test sample contained in the test sample cavity 247. One aspect of the present invention includes an axially hollow lower collet 205, a transparent lower rod 210, and a curing energy coupling 141 between the curing activation device 140 and the lower collet 205. Curing energy then flows from the curing activation device 140 to the test sample cavity 247 by traveling through the curing energy coupling 141, through the hollow lower collet 205, and through the transparent lower rod 210. An alternative method would be to introduce the curing energy horizontally from the side of the test sample cavity 247 by using a transparent mold member 245.

Another aspect of the present invention could include the use of a transparent upper rod 235 that could further transmit the curing energy to a monitoring device contained within the upper member 400. Such device could be a phototransistor or photoresistor to detect the onset and termination of the application of curing energy, or to detect the intensity the curing energy.

As a polymer test sample cures in the test sample cavity 247, the polymer test sample changes volume, typically contracting. The test sample adheres to the upper and lower test fixture surfaces. As the polymer test sample changes volume during the curing process, the changing volume exerts force between the upper and lower test fixture surfaces, for example, the upper end face of the lower rod 210 and the lower end face of the upper rod 235. Various apparatus members transmit this force to the reference member 105 and the beam member 110, causing the relative position between the beam member 110 and the reference member 105 to change. This change in relative position correlates to the force developed by the polymer test sample. Therefore, measuring this change in relative position, combined with further calculation yields strain, load and stress information about the curing polymer test sample.

Accordingly, an additional aspect of the present invention includes a beam position measuring device 130. The beam position measuring device 130 measures relative position or change in relative position between the reference member 105 and the beam member 110. The beam position measuring device 130 may include, for example, an electronic position transducer, such as a linear variable differential transformer (LVDT) 250. FIGS. 6 and 7 illustrate an LVDT 250 coupled to the upper fixture test bracket 400. An alternative method would be to couple the LVDT 250 to the reference member 105.

Figure 8A:
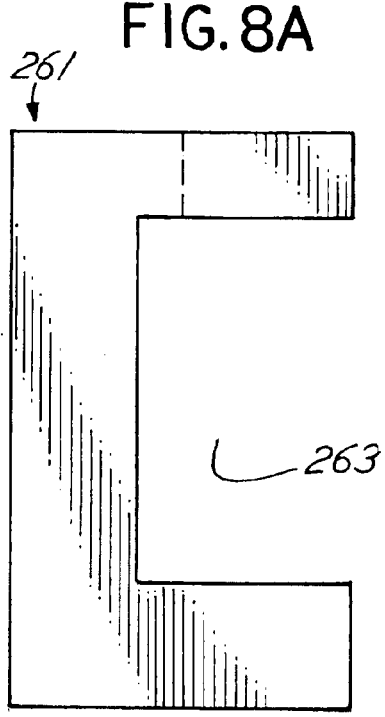
FIGS. 8A–8C show frontal, side and top views of a micrometer mounting bracket.
Figure 8B:
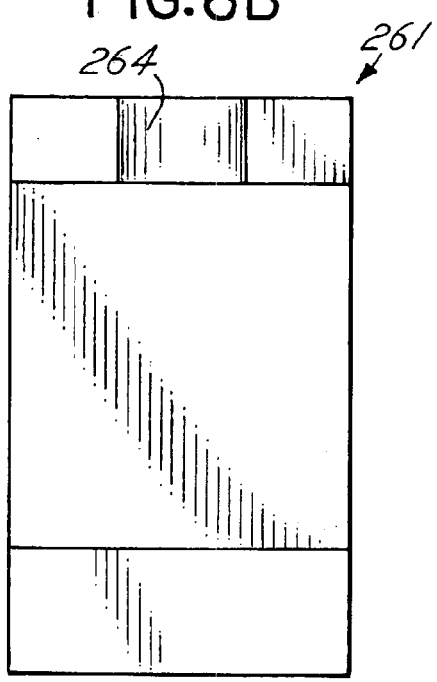
Figure 8C:
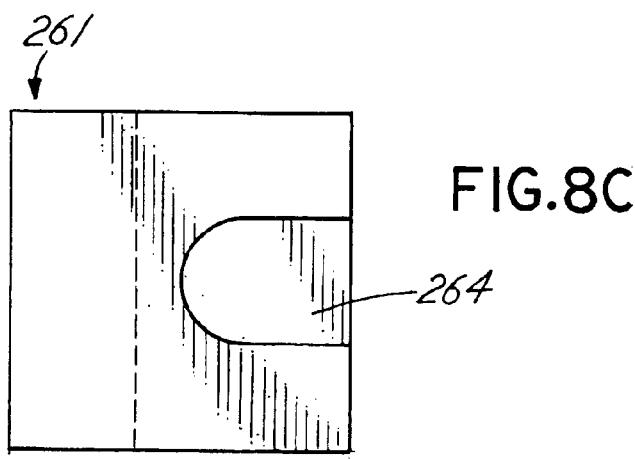

The LVDT 250, or other electronic position transducer, may have a preferred operating position. To provide for configuring the LVDT 250 in its preferred operating position, a micrometer 260 and micrometer mounting bracket 261 couple the LVDT 250 to the reference member 105. FIGS. 8A–8C show drawings of the micrometer mounting bracket 261. The micrometer mounting bracket 261 is rigidly coupled to the reference member 105. The micrometer mounting bracket 261 includes a micrometer holding cavity 263 in which the micrometer 260 sits, and a micrometer shaft cutout 264 through which a shaft 265 from the micrometer 260 extends to the LVDT 250. The micrometer shaft 265 is then coupled to a moving member 256 of the LVDT 250. An alternative method is to have the LVDT coupled to the reference member 105 with the moving member 256 coupled to the upper member 400 or to the beam member 110 in a manner so as to be adjustable in length and position in reference to the LVDT 250.

An aspect of the present invention includes a measurement monitor 300, as illustrated generally in FIG. 9. The measurement monitor 300 may, for example, be a general purpose computer with a monitor 905, keyboard 910 and processor tower 915. The measurement monitor 300 may be communicatively coupled to the beam position measuring device 130 by, for example, an electrical cable 920.

The measurement monitor 300 is preferably configured to track measurement readings from the beam position measuring device 130 over a time period during the curing of a polymer sample. The time period may vary according to the needs of a particular experiment, from the entire curing period for a polymer test sample to a single sample at a point in time during the curing period.

The measurement monitor 300 may also be controllably coupled to the curing activation device 140 such that the measurement monitor 300 can control the operation of the curing activation device 140, thereby providing automated control of the testing process.

The measurement monitor 300 may also be couple to other sensors and transducers to monitor and record such things as the onset, completion and intensity of curing energy, the temperature of the sample, or other response being measured in the sample or measurement system.

The measurement monitor 300 may further process measurement information that the measurement monitor 300 obtains from the beam position measuring device 130 and other sensors. The measurement monitor 300 may, for example, calculate force and stress due to the curing polymer sample as a function of the measurement information obtained from the beam position measuring device 130. The measurement monitor 300 may calculate load force by multiplying a change in beam position by a load/deflection ratio for the beam member 110. The measurement monitor 300 may calculate stress by dividing the load force by cross-sectional surface area of the test sample. The measurement monitor 300 may calculate and record the time when curing energy first enters the sample and when it stops, the intensity of the curing energy, and the temperature of the sample.

The measurement monitor 300 provides compiled and calculated test results to an operator. The measurement monitor 300 may provide compiled and calculated test information to an operator through a variety of media, for example, a tabular or graphical representation on the monitor 905 or a computer generated printout.

Figure 10E:
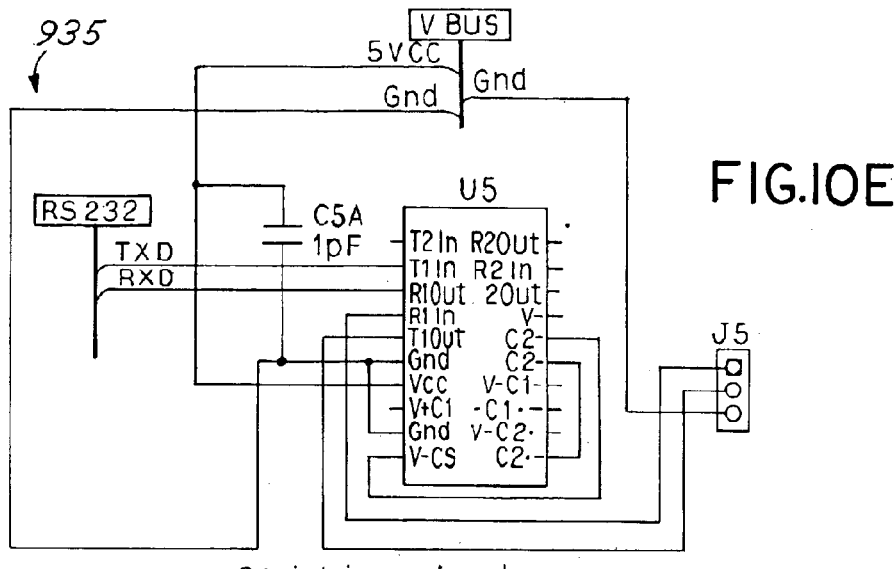
Figure 10F:
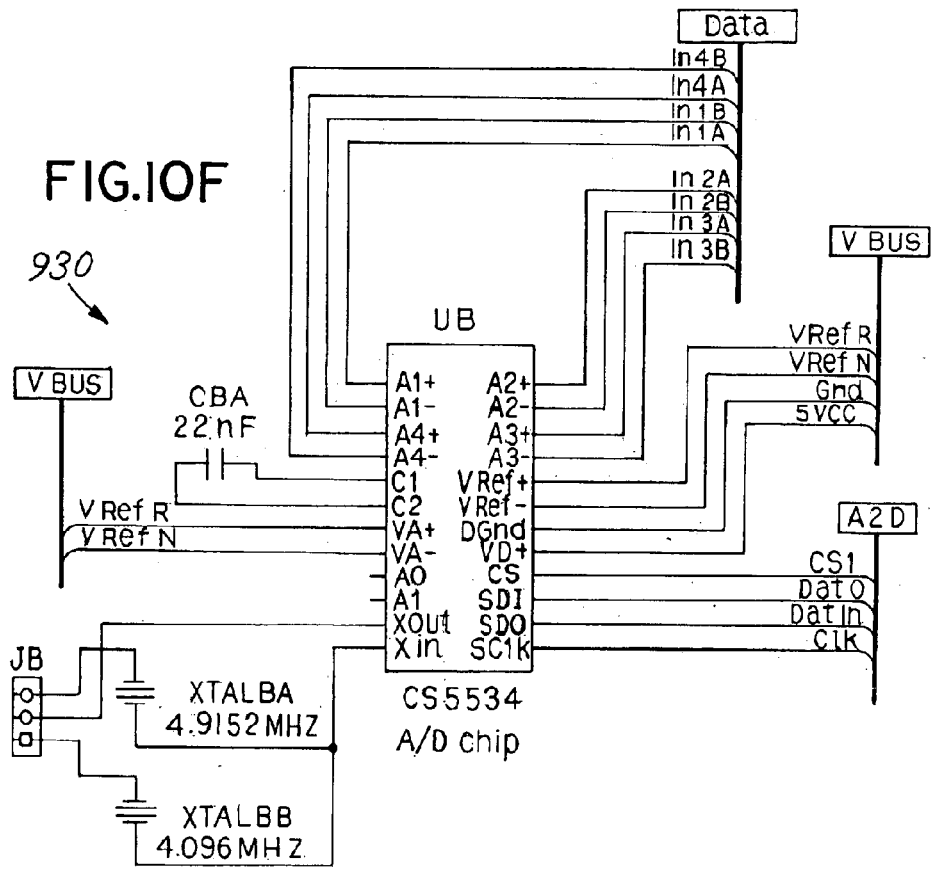
Figure 10G:
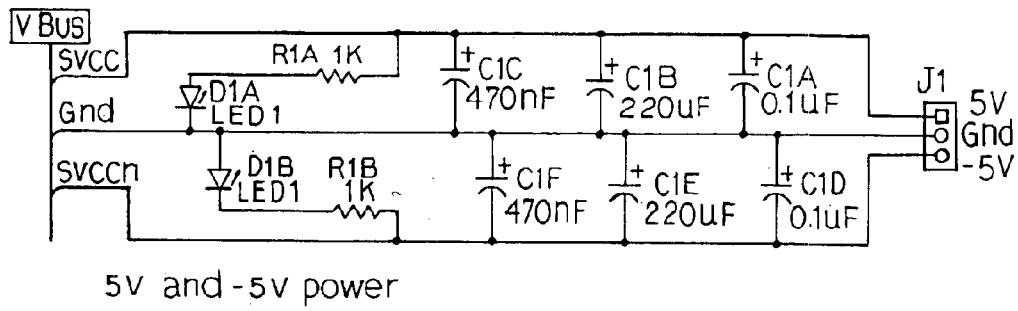
Figure 10H:
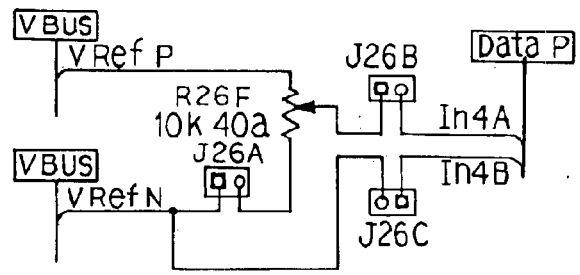
Figure 10I:
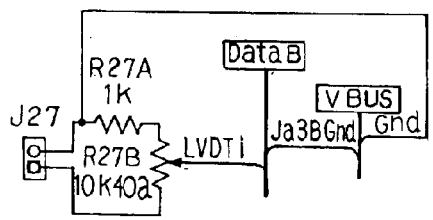
Figure 10K:
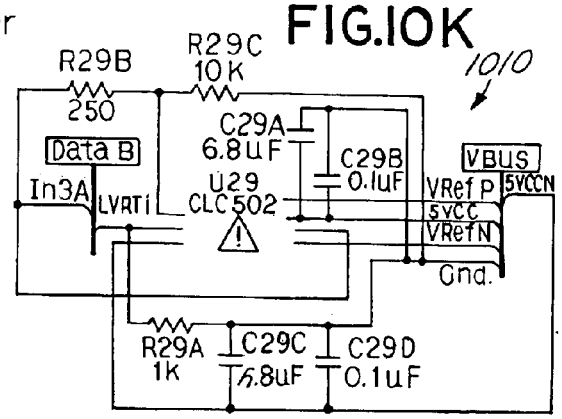
Figure 10J:
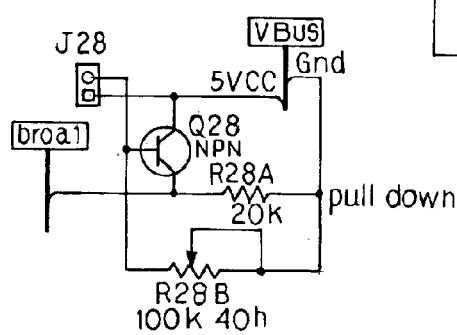
Figure 10L:
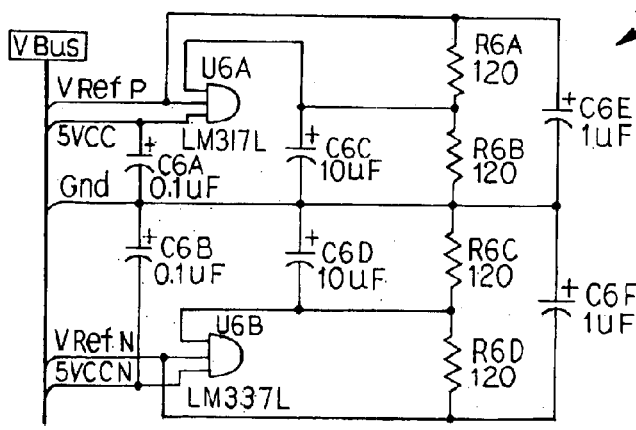

The measurement monitor 300 may include a variety of supporting circuitry to assist in monitoring and controlling the test apparatus. FIGS. 10A–10L contain schematics for various exemplary electrical support circuits. The support circuits include a power supply circuit 900, a voltage reduction circuit 905, and a thermistor reference voltage circuit 907. An LVDT voltage clamp 1010 and LVDT voltage divider 920 circuit support operation of the LVDT. An analog-to-digital circuit 930 and serial I/O circuit 935 support test measurement data acquisition and test control performed by the processor circuit 940. FIG. 10B also contains a lamp trigger circuit 945 to utilize in interfacing a curing lamp to the measurement monitor 300. Alternative electrical circuitry and computer software necessary to support the interfacing of sensors to data acquisition apparatus are generally well-known in the art of computer controlled or monitored experimentation.

Regarding the operation of the tensometer 100, prior to use of the tensometer 100, an operator should calibrate the tensometer 100. As mentioned previously, to determine load force and stress due to a curing test sample, the measurement monitor 300 converts a beam position measurement into a load or stress number. To perform this calculation, the monitor utilizes the load/deflection coefficient for the beam member 110 in its current position or the current position of the upper collet 230 along the length of the beam member 110. An operator may also utilize the load/deflection coefficient to determine the desired cantilever length of the beam member 110.

Figure 11:
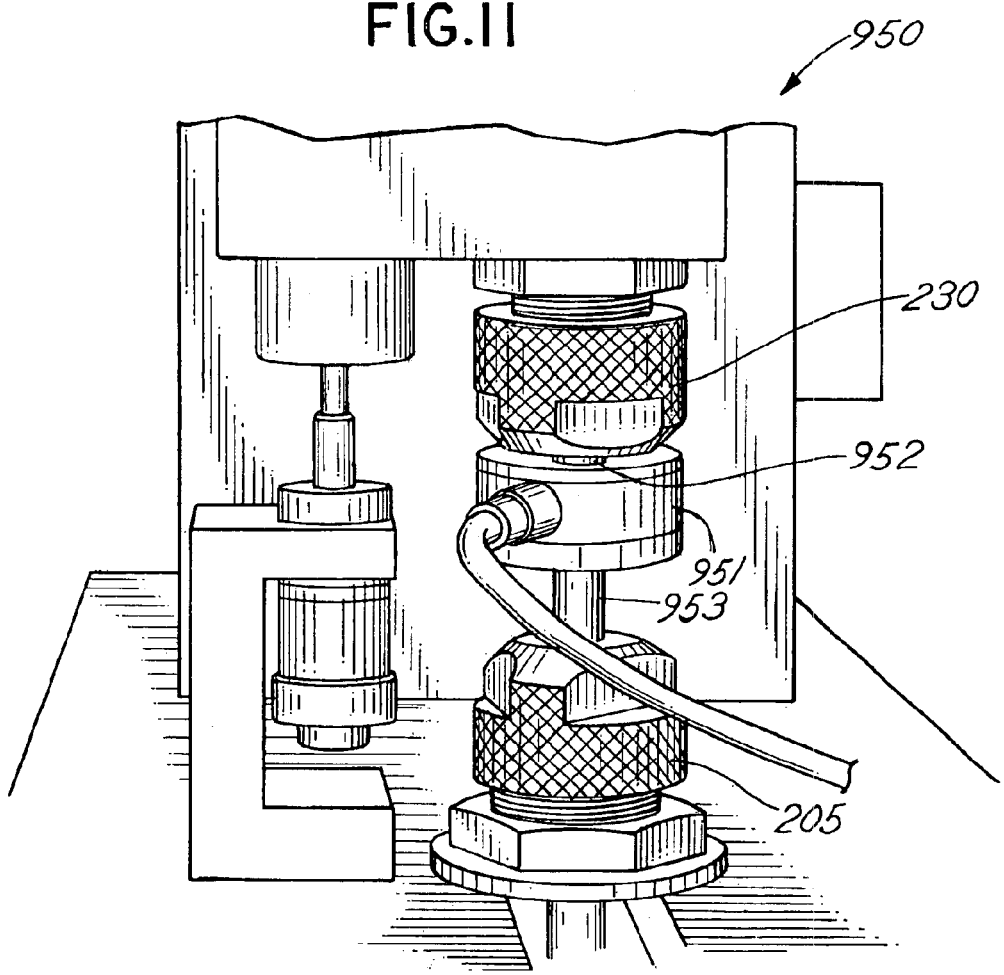
FIG. 11 shows an end view of the tensometer configured for calibration.

FIG. 11 illustrates calibration apparatus 950 that an operator may utilize to determine the load/deflection ratio for the beam member 110 in its current position. The calibration apparatus includes a calibrated tensile load cell 951 utilized to measure a force applied to the beam member 110 relative to the reference member 105. The load cell 951 includes an upper shaft 952 extending into and coupled to the upper collet 230, and a lower shaft 953 extending into but not coupled to the lower collet 205. A pneumatic actuator is coupled to the lower collet 205. The piston rod of the pneumatic actuator is coupled to the lower shaft 953, which allows the pneumatic actuator to apply force to the lower shaft 953, and thus the load cell 951 and beam member 110.

In an exemplary calibration process, air or compressed gas is introduced into the pneumatic actuator with a pressure regulator until the output meter of the load cell 951 reads approximately five Newtons. The load, measured by the load cell 951 and output in Newtons, and the beam displacement, measured by the LVDT and output in Volts, are recorded. The load is then incrementally increased in five Newton increments, with the load and beam displacement being recorded at each increment. Table 1 below shows example test data for a lab calibration performed for a beam member 110 with a cantilever length of 15 cm. The first column represents the output of the load cell 951, the second column represents the LVDT output, and the third column includes the change in LVDT output relative to the initial zero-point measurement.

TABLE 1

Tensometer Calibration Data

| Load (Newtons) | Voltage (Volts) | Step Voltage Change (Volts) |
| --- | --- | --- |
| 0.0 | 0.218 | 0.000 |
| 5.4 | 0.230 | 0.012 |
| 10.0 | 0.240 | 0.022 |
| 15.1 | 0.251 | 0.033 |
| 19.7 | 0.260 | 0.042 |
| 24.8 | 0.271 | 0.053 |
| 31.7 | 0.286 | 0.068 |
| 35.6 | 0.295 | 0.077 |
| 40.3 | 0.305 | 0.087 |
| 46.0 | 0.318 | 0.100 |
| 50.2 | 0.327 | 0.109 |
| 54.9 | 0.337 | 0.119 |
| 59.8 | 0.348 | 0.130 |
| 66.3 | 0.362 | 0.144 |
| 70.8 | 0.372 | 0.154 |
| 75.7 | 0.383 | 0.165 |
| 83.9 | 0.401 | 0.183 |
| 86.5 | 0.407 | 0.189 |
| 90.9 | 0.417 | 0.199 |
| 96.2 | 0.428 | 0.210 |
| 97.9 | 0.433 | 0.215 |

After an operator gathers the load and beam displacement data, the operator performs mathematical regression, such as least sum of squares analysis, to determine a load/deflection ratio for the cantilever portion of the beam member 110. For the test data illustrated in Table 1, the mathematical regression resulted in a load/deflection ratio of 456.6 N/Volt. The operator may enter this coefficient into the measurement monitor 300 for use in converting beam displacement measurements into an indication of load for this particular beam configuration. The measurement monitor 300 has a user interface for inputting and outputting information, and the user interface is preferably set up in a standard user-friendly manner.

After setting the desired cantilever length of the beam member 110 or position of the upper collet 230 along the length of the beam and determining the load/deflection coefficient for the particular beam member 110 configuration, the operator configures the test fixture apparatus according to the desired geometry of the polymer test sample. The operator selects upper and lower test fixture surfaces 240, 215, which may include a lower end face of an upper rod 235 inserted into the upper collet 230 and an upper end face of a lower rod 210 inserted into the lower collet 105. The operator may align the lower test fixture surface 215 with the upper test fixture surface 240 by moving the lower test fixture member 120 along the fixture translation feature 127 and securing the lower test fixture member 120 in the desired location.

The operator may further adjust the thickness of the polymer test sample by adjusting the gap between the upper test fixture surface 240 and the lower test fixture surface 215. For example, the operator may adjust the gap between the lower end face of the upper rod 235 and the upper end face of the lower rod 210 by adjusting the longitudinal position of the rods 210, 235 in the collets 205, 230. The operator may utilize a feeler gauge in this process to promote test process repeatability. During this gap-setting process, the operator may insert flexible tubing 246 over the rods 210, 235, whereby the flexible tubing 246 and ends of the rods 210, 235 define a test sample cavity 247. Alternatively, the operator may utilize a variety of mold member 245 configurations to provide the desired polymer test sample geometry and test conditions.

After forming the desired test sample cavity 247, the operator inserts polymer test material into the test sample cavity 247. Such insertion may include injecting the polymer test material into the test sample cavity through or around the walls of the flexible tubing 246. Alternatively, a mold member 245 may have various features known in the art for injecting material into a mold prior to curing. The operator may then insert other sample monitoring devices, such as thermocouples, thermistors or fiber optic cables through the mold member 245 and into or adjacent to the sample cavity 247.

To initiate the test process, the operator initiates curing of the polymer test sample and the acquisition of time and beam deflection information. The operator may initiate curing of the test sample, for example, by manually exposing the test sample to curing energy from a curing activation device 140 or by initiating a test sequence at the measurement monitor 300, which in turn automatically controls the operation of the curing activation device 140. The operator may adjust the time period over which the measurement monitor 300 tracks the deflection of the beam member 110, preferably tracking the deflection of the beam member 110 throughout the curing process. During the test process, the measurement monitor 300 preferably also calculates beam load and/or test sample stress using the load/deflection ratio determined earlier during the calibration process. The measurement monitor may also track and record sample strain, onset, termination and intensity of the activation energy, sample temperature and other monitored sample data.

The measurement monitor 300 may convey the test results to the operator in textual or graphical form. The measurement monitor 300 may provide the test results to the operator on a display device 905 or via a hard copy printout. Following are the results of three example polymer test sequences.

EXAMPLE 1

The first test example involved curing a commercially available dental composite (TPH®, Dentsply International) by curing the sample for 240 seconds using a dental curing light for curing activation. The test sample was 4 mm in diameter and 4.0 mm thick, simulating the approximate side and bonded surface area of a typical three surface dental filling on a bicuspid tooth.

For set-up of the tensometer 100, the cantilever portion of the beam member 110 was set to 12.65 cm, which resulted in a maximum beam flexure of approximately 20 micrometers during curing. This displacement was chosen as midrange from values reported in several clinical studies of cuspal deflection during curing of similar restorations.

The tensometer 100 was further configured using two 4 mm diameter quartz rods for the upper and lower rods 235, 210. The end faces of the quartz rods were polished and treated with two coats of a silane coupling agent to enhance polymer adhesion. The rods were inserted into the collets 205, 230 and flexible tubing 246 consisting of a 1.5 cm length of Tygon tubing slipped over the rods 210, 235. The operator spaced the rods 210, 235 using a 4 mm spacer and secured the rods 210, 235 into position by tightening the collets 205, 230. After securing the rods 210, 235, the operator slid the flexible tubing 246 over both rods 210, 235, bridging the gap between the two rods 210, 235 and completing the formation of the test sample cavity 247.

After so forming the test sample cavity 247, the operator injected the test material through a small hole in the side of the flexible tubing 246. The operator then utilized the micrometer 260 to set the electronic position transducer 250 (in this case, a LVDT) to the desired starting position within its measurement range. The operator positioned the curing activation device 140 (in this case, a dental curing light) under the lower end of the lower rod 210.

The operator next entered operating parameters into the measurement monitor 300 user interface. The operating parameters included test sample dimensions, the beam load/deflection ratio, and light cure time. The operator then initiated the test and the measurement monitor 300 then automatically controlled the test. The measurement monitor 300 turned the curing light on for 240 seconds and began taking data when an attached phototransistor detected the light from the curing lamp.

Figure 12:
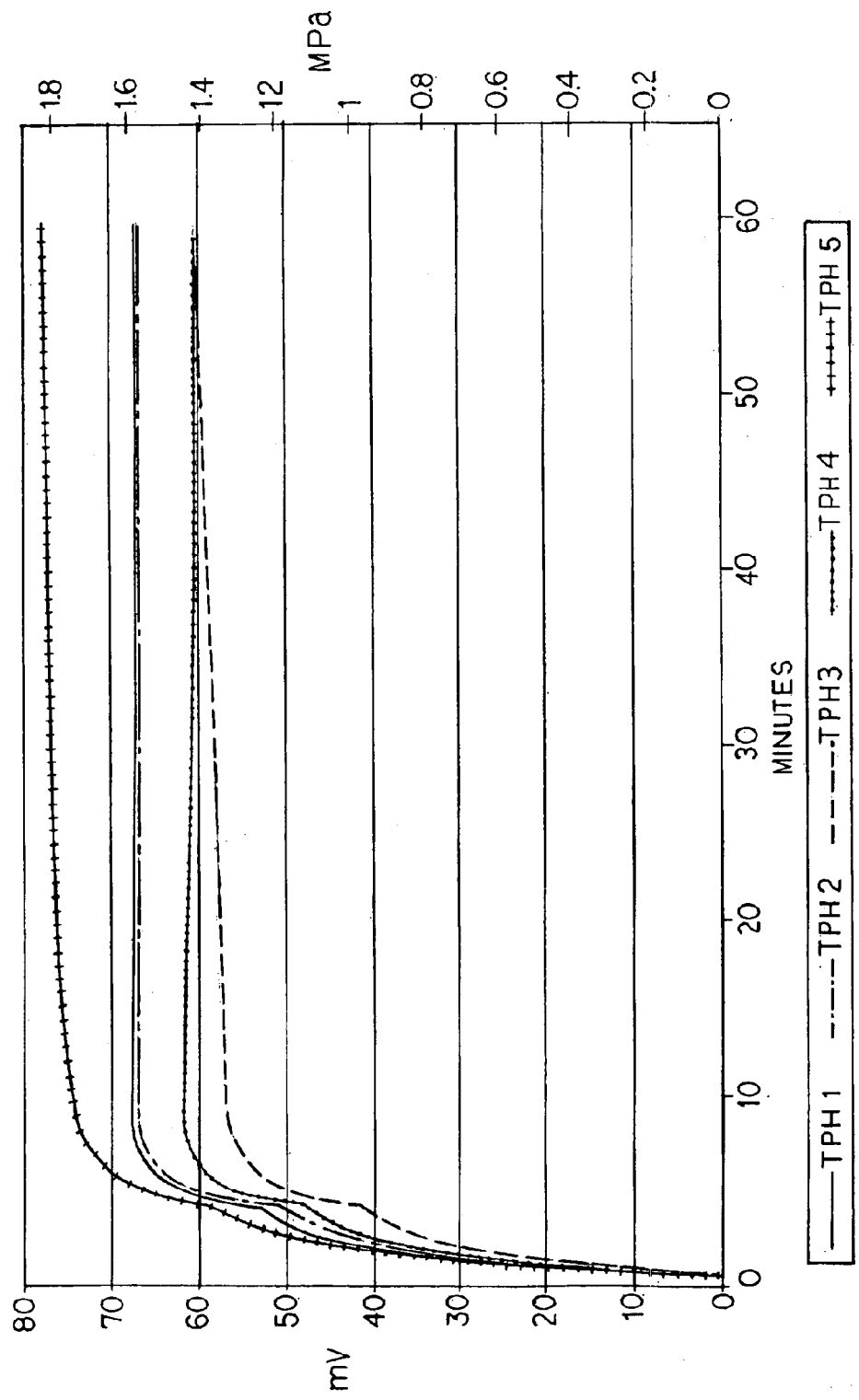
FIG. 12 is a graphical illustration of the results of test example 1.

During the sample curing process, the measurement monitor 300 collected time and beam displacement data (from the LVDT) for an hour. The measurement monitor 300 displayed and printed a computer-generated graph of beam displacement, load, and stress versus time. The measurement monitor 300 also saved the acquired test data in a test file for later reference. The operator performed five such tests, and FIG. 12 shows a graphical representation of the results. The left vertical edge of the graph is labeled with voltage readings (in mV) from the LVDT, and the right vertical edge of the graph is labeled with calculated stress (in mPa). The Horizontal axis of the graph is representative of the one hour duration of the tests.

EXAMPLE 2

Figure 13:
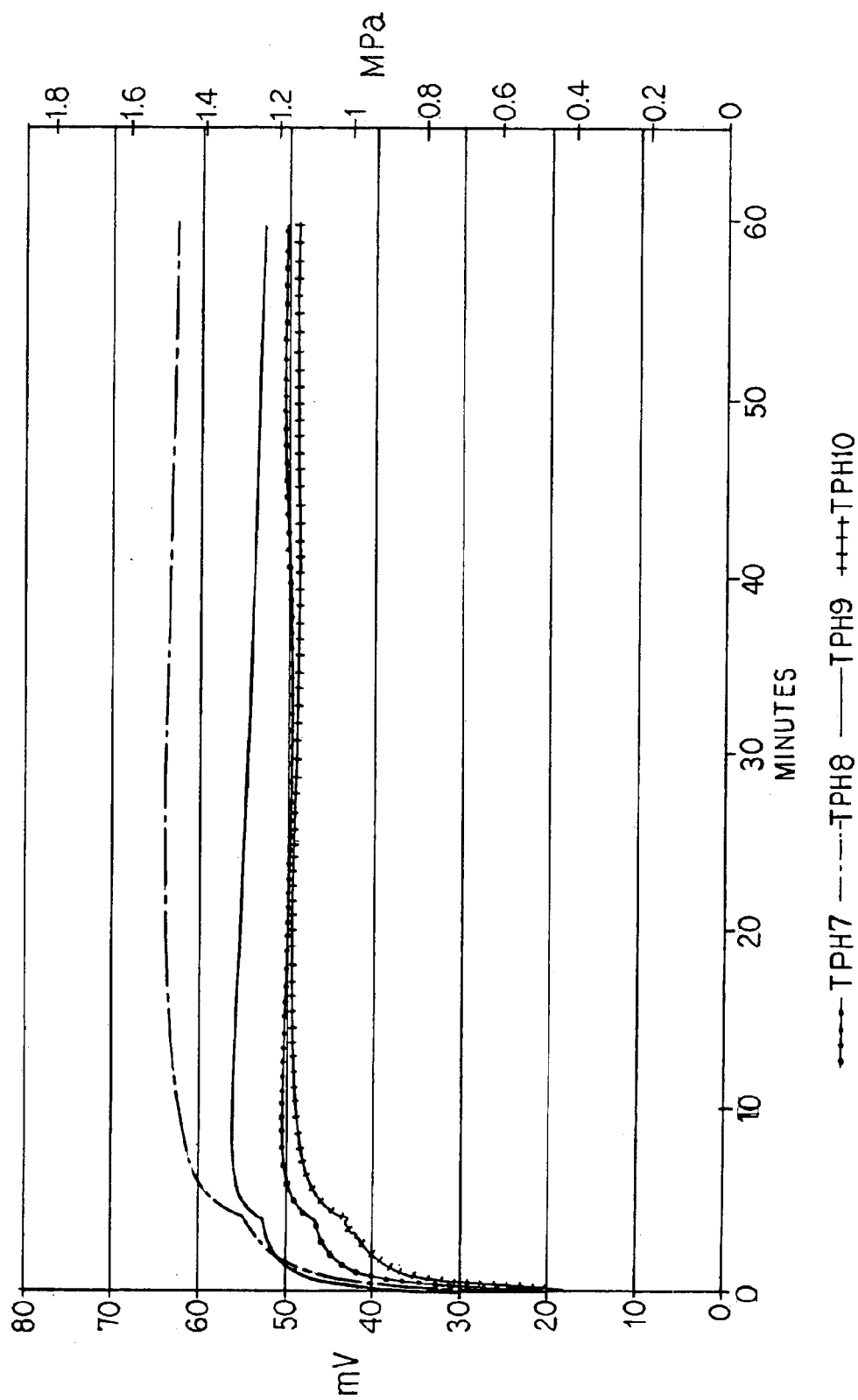
FIG. 13 is a graphical illustration of the results of test example 2.

The operator repeated the experiment of example 1, changing only the sample length (i.e., the gap between the quartz rods) to be 0.5 mm. This change in sample length resulted in a C-factor 8 times greater than that for example 1. FIG. 13 illustrates the results for four tests run under this new C-factor. Comparing the results from example 1 and example 2, the results indicate that longer samples with lower C-factors result in higher ultimate stress.

EXAMPLE 3

Figure 14:
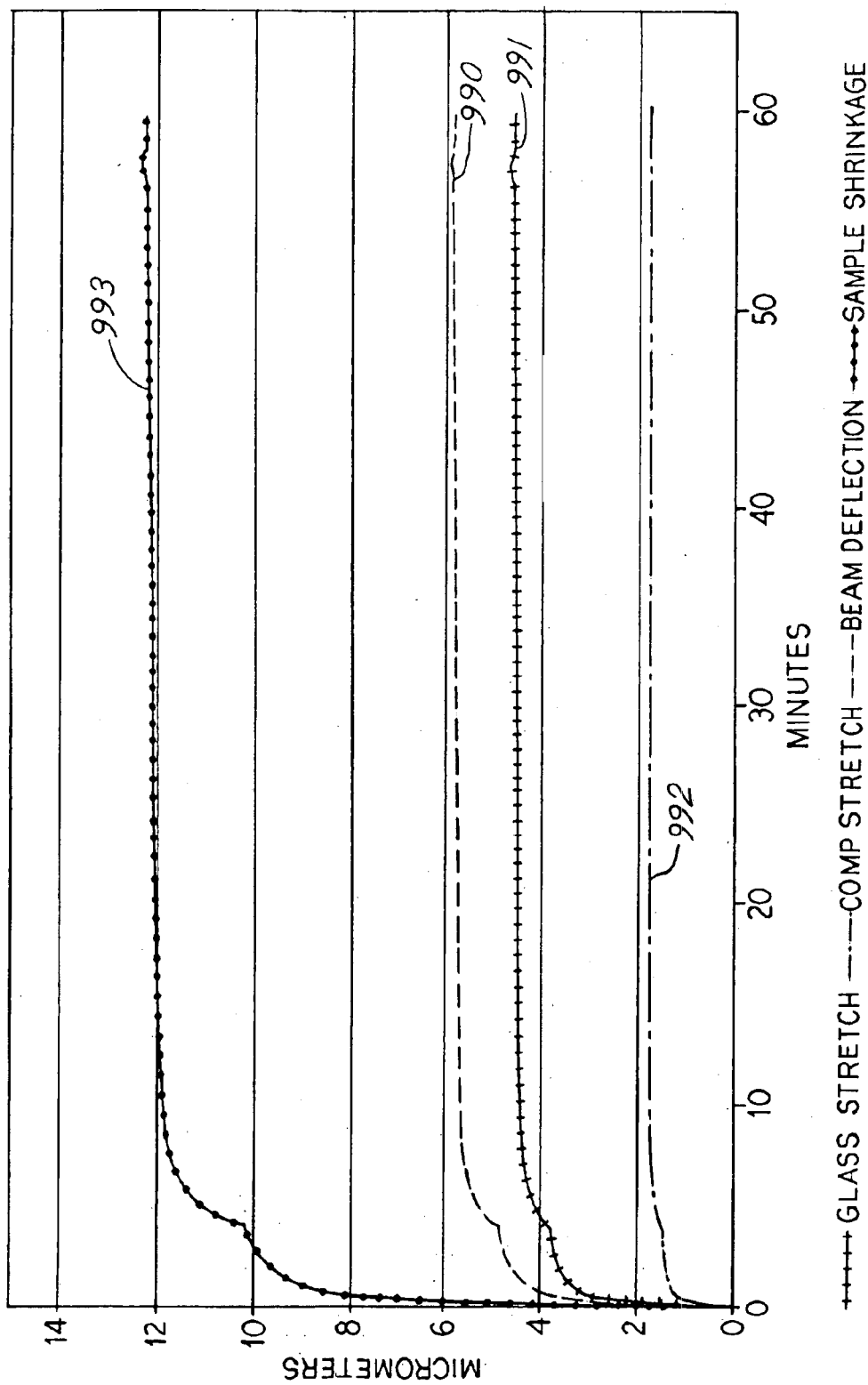
FIG. 14 is a graphical illustration of the results of test example 3.

Lastly, the operator conducted a similar experiment using a different test material (P60®, 3M) and a sample length of 1 mm. The operator performed one test run, resulting in the beam deflection plot 990, shown in FIG. 14. The operator configured the test apparatus to calculate the compliance of various tensometer 100 components. For example, the load, area, length and modulus values for the quartz (glass) rods were used to determine the elongation 991, under stress, of the rods. The composite sample elongation 992 was similarly calculated. Combining the measured beam deflection 990 and the calculated rod stretch 991 and the composite shrinkage 992 results in the total sample shrinkage 993. The test results were found to be close to the expected shrinkage for the particular composite.

While particular elements, aspects and applications of the present invention have been shown and described, it will be understood, of course, that the invention is not limited thereto since modifications may be made by those skilled in the art, particularly in light of the foregoing teachings. It is therefore contemplated by the appended claims to cover such modifications as incorporate those features that come within the spirit and scope of the invention.

What is claimed is:

1. A polymer shrinkage tensometer, comprising:
a reference member;
a first fixture member coupled to the reference member and having a first fixture surface;
a second fixture member having a second fixture surface in opposed and spaced relation to the first fixture surface;
a beam member coupled to the reference member and the second fixture member such that the beam member moves relative to the reference member in response to a force applied between the first fixture surface and the second fixture surface;
a beam position measuring device coupled to the reference member and the beam member such that the beam position measuring device measures relative position between the beam member and the reference member; and
a measurement monitor coupled to the beam position measuring device, the measurement monitor tracking the relative position between the beam member and the reference member over a time period.

2. The polymer shrinkage tensometer of claim 1, wherein:
the reference member comprises a fixture translation feature running substantially parallel with the beam member; and
the first fixture member is coupled to the fixture translation feature.

3. The polymer shrinkage tensometer of claim 1, wherein: the first fixture member comprises:
a first collet coupled to the reference member; and
a first rod protruding axially from and secured by the first collet; and
the first fixture surface comprises the end face of the first rod protruding from the first collet;
the second fixture member comprises:
a second collet coupled to the beam member;
second rod protruding axially from and secured by the second collet; and
the second fixture surface comprises the end face of the second rod protruding from the second collet.

4. The polymer shrinkage tensometer of claim 1, further comprising a beam mount coupling the beam member to the reference member such that the length of the beam member extending from the beam mount to the second fixture member is adjustable.

5. The polymer shrinkage tensometer of claim 3, further comprising said second collet coupled to the beam member such that the position of said second collet can be moved along the length of the beam and fixed at any position along the length of the beam.

6. The polymer shrinkage tensometer of claim 1, wherein the beam position measuring device comprises an electronic position transducer coupled to the reference member and the beam member.

7. The polymer shrinkage tensometer of claim 1, wherein the measurement monitor further tracks a load acting between the first fixture member and the second fixture member as a function of the relative position between the beam member and the reference member over the time period.

8. The polymer shrinkage tensometer of claim 1, wherein the measurement monitor further tracks stress acting on the first fixture surface and the second fixture surface as a function of the relative position between the beam member and the reference member over the time period.

9. The polymer shrinkage tensometer of claim 1, further comprising a mold member coupled to at least one of the first and second fixture members, the mold member designed to hold polymer material while the polymer material cures.

10. The polymer shrinkage tensometer of claim 3, further comprising flexible tubing coupled to the protruding ends of the first and second rods.

11. The polymer shrinkage tensometer of claim 1, further comprising a curing activation device disposed to facilitate the curing of a polymer material inserted between the first fixture surface and the second fixture surface, the curing activation device operationally coupled to the measurement monitor.

12. The polymer shrinkage tensometer of claim 3, further comprising a curing activation device coupled to the first collet to provide curing energy to polymer material inserted between the first and second fixture surfaces, and wherein:
the first collet is hollow to allow the curing energy from the curing activation device to flow through the first collet to the first rod; and
the first rod is substantially transparent to allow the curing energy from the curing activation device to flow through the first rod to the polymer material.

13. The polymer shrinkage tensometer of claim 1 further comprising a monitoring device to detect the onset of curing energy delivered to the sample.

14. The tensometer of claim 13 wherein said monitoring device comprises means to measure the termination of curing energy and intensity of curing energy delivered to the sample.

15. The polymer shrinkage tensometer of claim 1 further comprising a temperature monitoring device to measure the sample temperature before, during and after curing of the polymer.

16. The polymer shrinkage tensometer of claim 1 further comprising a split curing cell disposed about the space between the first and second fixture surfaces, the split curing cell providing for temperature or atmospheric control during polymer curing.

17. A method for measuring forces occurring during polymer material curing, the method comprising:
providing a first fixture member having a first fixture surface for engagement generally with a polymer material;
providing a second fixture member having a second fixture surface for engagement generally with a polymer material;
positioning the first and second fixture members such that the second fixture surface is in a generally opposed and spaced relation to the first fixture surface;
supporting the second fixture member on a beam member that flexes in response to a force applied between the first fixture surface and the second fixture surface;
inserting uncured polymer material into the space between the first fixture surface and the second fixture surface, the uncured polymer material engaging the first fixture surface and the second fixture surface;
subjecting the uncured polymer material to conditions that facilitate hardening thereof;
measuring flexure of the beam member during hardening of the polymer material; and
tracking the measured flexure of the beam member during hardening of the polymer material.

18. The method of claim 17, further comprising adjusting the load versus flex characteristics of the beam member by adjusting the length of the beam member that flexes in response to a force applied between the first fixture surface and the second fixture surface.

19. The method of claim 17, further comprising adjusting the load versus flex characteristics of the beam member by adjusting the position of said second fixture along the length of the beam.

20. The method of claim 17, further comprising providing a mold member coupled to at least one of the first and second fixture members, and wherein inserting uncured polymer material further comprises injecting the uncured polymer material into the space bounded by the first fixture surface, the second fixture surface and the mold member.

21. The method of claim 17, further including changing the dimensions of the space bounded by the first fixture surface, the second fixture surface and the mold member.

22. The method of claim 17, wherein measuring flexure of the beam member comprises measuring flexure of the beam member with a beam position measuring device electrically coupled to a measurement monitor.

23. The method of claim 21, wherein subjecting the uncured material to conditions comprises applying curing energy to the polymer material using a curing activation device operationally coupled to the measurement monitor.

24. The method of claim 21, wherein tracking the measured flexure of the beam member comprises acquiring time and beam flexure information during hardening of the polymer material.

25. The method of claim 21, wherein tracking the measured temperature of the sample comprises acquiring time and temperature information during hardening of the polymer material.

26. The method of claim 21, wherein tracking the onset, termination and/or intensity of curing energy comprises acquiring time and curing energy information during hardening of the polymer material.

27. The method of claim 24, further comprising tracking beam load versus time by calculating the beam load using the acquired beam flexure information.

28. The method of claim 24, further comprising tracking polymer stress versus time by calculating the polymer stress using the acquired beam flexure information.

29. The method of claim 24, further comprising tracking polymer strain versus time by calculating the polymer strain using the acquired beam flexure information.

30. A polymer shrinkage tensometer, comprising:
a reference member;
a first fixture member coupled to the reference member and having a first fixture surface;
a second fixture member having a second fixture surface in opposed and spaced relation to the first fixture surface;
a beam member coupled to the reference member and the second fixture member such that the beam member moves relative to the reference member in response to a force applied between the first fixture surface and the second fixture surface;
a beam position measuring device coupled to the reference member and the beam member such that the beam position measuring device measures relative position between the beam member and the reference member;
a measurement monitor coupled to the beam position measuring device, the measurement monitor tracking the relative position between the beam member and the reference member over a time period; and
a beam mount coupling the beam member to the reference member such that the length of the beam member extending from the beam mount to the second fixture member is adjustable.

31. The polymer shrinkage tensometer of claim 30, wherein:
the reference member comprises a fixture translation feature running substantially parallel with the beam member; and the first fixture member is coupled to the fixture translation feature.

32. The polymer shrinkage tensometer of claim 30, wherein:
the first fixture member comprises:
a first collet coupled to the reference member;
a first rod protruding axially from and secured by the first collet; and
the first fixture surface comprises the end face of the first rod protruding from the first collet;
the second fixture member comprises:
a second collet coupled to the beam member;
second rod protruding axially from and secured by the second collet; and
the second fixture surface comprises the end face of the second rod protruding from the second collet.

33. The polymer shrinkage tensometer of claim 30, further comprising a second collet coupled to the beam member such that the position of said second collet can be moved along the length of the beam and fixed at any position along the length of the beam.

34. The polymer shrinkage tensometer of claim 30, wherein the beam position measuring device comprises an electronic position transducer coupled to the reference member and the beam member.

35. The polymer shrinkage tensometer of claim 30, wherein the measurement monitor further tracks a load acting between the first fixture member and the second fixture member as a function of the relative position between the beam member and the reference member over the time period.

36. The polymer shrinkage tensometer of claim 30, wherein the measurement monitor further tracks stress acting on the first fixture surface and the second fixture surface as a function of the relative position between the beam member and the reference member over the time period.

37. The polymer shrinkage tensometer of claim 30, further comprising a mold member coupled to at least one of the first and second fixture members, the mold member designed to hold polymer material while the polymer material cures.

38. The polymer shrinkage tensometer of claim 32, further comprising flexible tubing coupled to the protruding ends of the first and second rods.

39. The polymer shrinkage tensometer of claim 30, further comprising a curing activation device disposed to facilitate the curing of a polymer material inserted between the first fixture surface and the second fixture surface, the curing activation device operationally coupled to the measurement monitor.

40. The polymer shrinkage tensometer of claim 32, further comprising a curing activation device coupled to the first collet to provide curing energy to polymer material inserted between the first and second fixture surfaces, and wherein:
the first collet is hollow to allow the curing energy from the curing activation device to flow through the first collet to the first rod; and
the first rod is substantially transparent to allow the curing energy from the curing activation device to flow through the first rod to the polymer material.

41. The polymer shrinkage tensometer of claim 30 further comprising a monitoring device to detect the onset of curing energy delivered to the sample.

42. The tensometer of claim 41 wherein said monitoring device comprises means to measure the termination of curing energy and intensity of curing energy delivered to the sample.

43. The polymer shrinkage tensometer of claim 30 further comprising a temperature monitoring device to measure the sample temperature before, during and after curing of the polymer.

44. The polymer shrinkage tensometer of claim 30 further comprising a split curing cell disposed about the space between the first and second fixture surfaces, the split curing cell providing for temperature or atmospheric control during polymer curing.

45. A polymer shrinkage tensometer, comprising:
a reference member;
a first fixture member coupled to the reference member and having a first fixture surface;
a second fixture member having a second fixture surface in opposed and spaced relation to the first fixture surface;
a beam member coupled to the reference member and the second fixture member such that the beam member moves relative to the reference member n response to a force applied between the first fixture surface and the second fixture surface;
a beam position measuring device coupled to the reference member and the beam member such that the beam position measuring device measures relative position between the beam member and the reference member;
a measurement monitor coupled to the beam position measuring device, the measurement monitor tracking the relative position between the beam member and the reference member over a time period, and
a first collet coupled to the beam member such that the position of said first collet can be moved along the length of the beam member and fixed at a position along the length of the beam member.

46. The polymer shrinkage tensometer of claim 45, wherein:
the reference member comprises a fixture translation feature running substancially parallel with the beam member; and
the first fixture member is coupled to the fixture translation feature.

47. The polymer shrinkage tensometer of claim 45, wherein:
the first fixture member comprises:
a second collet coupled to the reference member;
a first rod protruding axially from and secured by the second collet; and
the first fixture surface comprises the end face of the first rod protruding from the second collet;
the second fixture member comprises:
a second rod protruding axially from and secured by the first collet; and
the second fixture surface comprises the end face of the second rod protruding from the first collet.

48. The polymer shrinkage tensometer of claim 45, wherein the beam position measuring device comprises an electronic position transducer coupled to the reference member and the beam member.

49. The polymer shrinkage tensomeler of claim 45, wherein the measurement monitor further tracks a load acting between the first fixture member and the second fixture member as a function of the relative position between the beam member and the reference member over the time period.

50. The polymer shrinkage tensometer of claim 45, wherein the measurement monitor further tracks stress acting on the first fixture surface and the second fixture surface as a function of the relative position between the beam member and the reference member over the time period.

51. The polymer shrinkage tensometer of claim 45, further comprising a mold member coupled to at least one of the first and second fixture members, the mold member designed to hold polymer material while the polymer material cures.

52. The polymer shrinkage tensometer of claim 47, further comprising flexible tubing coupled to the protruding ends of the first and second rods.

53. The polymer shrinkage tensometer of claim 45, further comprising a curing activation device disposed to facilitate the curing of a polymer material inserted between the first fixture surface and the second fixture surface, the curing activation device operationally coupled to the measurement monitor.

54. The polymer shrinkage tensometer of claim 47, further comprising a curing activation device coupled to the second collet to provide curing energy to polymer material inserted between the first and second fixture surfaces, and wherein:
the second collet is hollow to allow the curing energy from the curing activation device to flow through the second collet to the first rod; and
the first rod is substantially transparent to allow the curing energy from the curing activation device to flow through the first rod to the polymer material.

55. The polymer shrinkage tensometer of claim 45 further comprising a monitoring device to detect the onset of curing energy delivered to the sample.

56. The tensometer of claim 55 wherein said monitoring device comprises means to measure the termination of curing energy and intensity of curing energy delivered to the sample.

57. The polymer shrinkage tensometer of claim 45 further comprising a temperature monitoring device to measure the sample temperature before, during and after curing of the polymer.

58. The polymer shrinkage tensometer of claim 45 further comprising a split curing cell disposed about the space between the first and second fixture surfaces, the split curing cell providing for temperature or atmospheric control during polymer curing.

59. A polymer shrinkage tensometer, comprising:
a reference member;
a first fixture member coupled to the reference member and having a first fixture surface;
a second fixture member having a second fixture surface in opposed and spaced relation to the first fixture surface;
a beam member coupled to the reference member and the second fixture member such that the beam member moves relative to the reference member in response to a force applied between the first fixture surface and the second fixture surface;
a beam position measuring device coupled to the reference member and the beam member such that the beam position measuring device measures relative position between the beam member and the reference member;
a measurement monitor coupled to the beam position measuring device, the measurement monitor tracking the relative position between the beam member and the reference member over a time period; and
a mold member coupled to at least one of the first and second fixture members, the mold member designed to hold polymer material while the polymer material cures.

60. The polymer shrinkage tensometer of claim 59, wherein:
the reference member comprises a fixture translation feature running substantially parallel with the beam member; and
the first fixture member is coupled to the fixture translation feature.

61. The polymer shrinkage tensometer of claim 59, wherein:
the first fixture member comprises:
a first collet coupled to the reference member;
a first rod protruding axially from and secured by the first collet; and
the first fixture surface comprises the end face of the first rod protruding from the first collet;
the second fixture member comprises:
a second collet coupled to the beam member;
second rod protruding axially from and secured by the second collet; and
the second fixture surface comprises the end face of the second rod protruding from the second collet.

62. The polymer shrinkage tensometer of claim 59, wherein the beam position measuring device comprises an electronic position transducer coupled to the reference member and the beam member.

63. The polymer shrinkage tensometer of claim 59, wherein the measurement monitor further tracks a load acting between the first fixture member and the second fixture member as a function of the relative position between the beam member and the reference member over the time period.

64. The polymer shrinkage tensometer of claim 59, wherein the measurement monitor further tracks stress acting on the first fixture surface and the second fixture surface as a function of the relative position between the beam member and the reference member over the time period.

65. The polymer shrinkage tensometer of claim 61, further comprising flexible tubing coupled to the protruding ends of the first and second rods.

66. The polymer shrinkage tensometer of claim 59, further comprising a curing activation device disposed to facilitate the curing of a polymer material inserted between the first fixture surface and the second fixture surface, the curing activation device operationally coupled to the measurement monitor.

67. The polymer shrinkage tensometer of claim 61, further comprising a curing activation device coupled to the first collet to provide curing energy to polymer material inserted between the first and second fixture surfaces, and wherein:
the first collet is hollow to allow the curing energy from the curing activation device to flow through the first collet to the first rod; and
the first rod is substantially transparent to allow the curing energy from the curing activation device to flow through the first rod to the polymer material.

68. The polymer shrinkage tensometer of claim 59 further comprising a monitoring device to detect the onset of curing energy delivered to the sample.

69. The tensometer of claim 68 wherein said monitoring device comprises means to measure the termination of curing energy and intensity of curing energy delivered to the sample.

70. The polymer shrinkage tensometer of claim 59 further comprising a temperature monitoring device to measure the sample temperature before, during and after curing of the polymer.

71. The polymer shrinkage tensometer of claim 59 further comprising a split curing cell disposed about the space between the first and second fixture surfaces, the split curing cell providing for temperature or atmospheric control during polymer curing.

72. A polymer shrinkage tensometer, comprising:
a reference member;
a first fixture member coupled to the reference member and having a first fixture surface;

a second fixture member having a second fixture surface in opposed and spaced relation to the first fixture surface;

a beam member coupled to the reference member and the second fixture member such that the beam member moves relative to the reference member in response to a force applied between the first fixture surface and the second fixture surface;

a beam position measuring device coupled to the reference member and the beam member such that the beam position measuring device measures relative position between the beam member and the reference member;

a measurement monitor coupled to the beam position measuring device, the measurement monitor tracking the relative position between the beam member and the reference member over a time period; and a curing activation device disposed to facilitate the curing of a polymer material inserted between the first fixture surface and the second fixture surface, the curing activation device operationally coupled to the measurement monitor.

73. The polymer shrinkage tensometer of claim 72, wherein:

the reference member comprises a fixture translation feature running substantially parallel with the beam member; and the first fixture member is coupled to the fixture translation feature.

74. The polymer shringage tensometer of claim 72, wherein the beam position measuring device comprises an electronic position transducer coupled to the reference member and the beam member.

75. The polymer shrinkage tensometer of claim 72, wherein the measurement monitor further tracks a load acting between the first fixture member and the second fixture member as a function of the relative position between the beam member and the reference member over the time period.

76. A polymer shrinkage tensometer, comprising:

a reference member;

a first fixture member coupled to the reference member and having a first fixture surface;

a second fixture member having a second fixture surface in opposed and spaced relation to the first fixture surface;

a beam member coupled to the reference member and the second fixture member such that the beam member moves relative to the reference member in response to a force applied between the first fixture surface and the second fixture surface;

a beam position measuring device coupled to the reference member and the beam member such that the beam position measuring device measures relative position between the beam member and the reference member;

a measurement monitor coupled to the beam position measuring device, the measurement monitor tracking the relative position between the beam member and the reference member over a time period; and a temperature monitoring device to measure the sample temperature before, during and after curing of the polymer.

77. A polymer shrinkage tensometer, comprising:

a reference member;

a first fixture member coupled to the reference member and having a first fixture surface;

a second fixture member having a second fixture surface in opposed and spaced relation to the first fixture surface;

a beam member coupled to the reference member and the second fixture member such that the beam member moves relative to the reference member in response to a force applied between the first fixture surface and the second fixture surface;

a beam position measuring device coupled to the reference member and the beam member such that the beam position measuring device measures relative position between the beam member and the reference member;

a measurement monitor coupled to the beam position measuring device, the measurement monitor tracking the relative position between the beam member and the reference member over a time period; and a monitoring device to detect the onset of curing energy delivered to the sample.

78. A polymer shrinkage tensometer, comprising:

a reference member;

a first fixture member coupled to the reference member and having a first fixture surface;

a second fixture member having a second fixture surface in opposed and spaced relation to the first fixture surface;

a beam member coupled to the reference member and the second fixture member such that the beam member moves relative to the reference member in response to a force applied between the first fixture surface and the second fixture surface;

a beam position measuring device coupled to the reference member and the beam member such that the beam position measuring device measures relative position between the beam member and the reference member;

a measurement monitor coupled to the beam position measuring device, the measurement monitor tracking the relative position between the beam member and the reference member over a time period; and a split curing cell disposed about the space between the first and second fixture surfaces, the split cell providing for temperature or atmospheric control during polymer curing.

79. A polymer shrinkage terisometer, comprising:

a reference member comprising a stationary base;

a first fixture member mounted to the reference member and having a first fixture surface;

a second fixture member having a second fixture surface in opposed and spaced relation to the first fixture surface;

a flexible cantilever beam member having a fixed end coupled to the reference member and a moveable end supporting the second fixture member in opposed relation to the first fixture member such that the beam member is moveable relative to the reference member in response to a force applied between the first fixture surface and the second fixture surface;

a beam position measuring device coupled to both the reference member and the beam member such that the beam position measuring device measures relative spacing between the fixture member surfaces; and a measurement monitor coupled to the beam position measuring device for measuring the spacing between the fixture member surfaces.

80. The tensometer of claim 79 wherein the measurement monitor comprises a device for measuring the spacing between the fixture member surfaces over a time period.

* * * * *